(12) United States Patent
Castellarnau et al.

(10) Patent No.: US 9,709,479 B2
(45) Date of Patent: Jul. 18, 2017

(54) METHOD AND APPARATUS FOR TRACKING CELL IDENTITY

(71) Applicant: MASSACHUSETTS INSTITUTE OF TECHNOLOGY, Cambridge, MA (US)

(72) Inventors: Marc Castellarnau, Charlestown, MA (US); Gregory Lee Szeto, Cambridge, MA (US); Darrell J. Irvine, Arlington, MA (US); John Christopher Love, Tbilisi, MA (US); Joel Voldman, Belmont, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 52 days.

(21) Appl. No.: 14/523,376

(22) Filed: Oct. 24, 2014

(65) Prior Publication Data
US 2015/0253237 A1   Sep. 10, 2015

Related U.S. Application Data

(60) Provisional application No. 61/895,732, filed on Oct. 25, 2013.

(51) Int. Cl.
| | | |
|---|---|---|
| *G01N 15/10* | (2006.01) | |
| *G01N 15/14* | (2006.01) | |
| *G01N 35/00* | (2006.01) | |
| *G01N 15/00* | (2006.01) | |

(52) U.S. Cl.
CPC ......... *G01N 15/1463* (2013.01); *G01N 15/10* (2013.01); *G01N 35/00732* (2013.01); *G01N 15/1484* (2013.01); *G01N 2015/008* (2013.01); *G01N 2015/0065* (2013.01); *G01N 2015/1006* (2013.01); *G01N 2015/149* (2013.01); *G01N 2035/00811* (2013.01); *G01N 2035/00831* (2013.01)

(58) Field of Classification Search
CPC .............. G01N 15/10; G01N 15/1463; G01N 15/1484; G01N 35/00732; G01N 2015/149; G01N 2015/1006; G01N 2035/00831
USPC ...... 422/82.05, 400; 435/174, 177, 180, 382
See application file for complete search history.

(56) References Cited

U.S. PATENT DOCUMENTS

| | | | | |
|---|---|---|---|---|
| 6,544,732 B1 * | 4/2003 | Chee | ....................... | B82Y 15/00 435/174 |
| 6,730,515 B2 * | 5/2004 | Kocher | ................ | B01J 19/0046 436/164 |
| 2012/0270295 A1 * | 10/2012 | Choo | ..................... | A61K 9/501 435/178 |

OTHER PUBLICATIONS

Sun and Voldman (15th International Conference on Miniaturized Systems for Chemistry and Life Sciences, Oct. 2-6, 2011, p. 693-695).*
Bristow et al, Blood 102(13):4479-4486, 2003.*
Falati et al, Nature Medicine 8(10):1175-1180, 2002.*
Goldman et al, Anal. Chem. 76:684-688, 2004.*

* cited by examiner

*Primary Examiner* — Kevin Hill
(74) *Attorney, Agent, or Firm* — Steptoe & Johnson LLP

(57) ABSTRACT

A method of tracking cell identity across analytical platforms uses stochastic barcoding (SB). SB uses a randomly generated code based on one or more of the number, color and position of beads encapsulated together with a set of cells of interest. SB use is demonstrated in an application where cells are transferred from a microwell array into a microtiter plate while keeping their identity, and obtained an average identification accuracy of 96% for transfer of 100 blocks. Model scaling of the method up to 1000 blocks demonstrated that SB is able to achieve approximately 90% accuracy.

22 Claims, 35 Drawing Sheets

(A) Cell viability (B) Genotyping (PCR) and phenotyping (RT-PCR)

(A)

(B)

METHOD AND APPARATUS FOR TRACKING CELL IDENTITY

CLAIM OF PRIORITY

This application claims the benefit of prior U.S. Provisional Application No. 61/895,732 filed on Oct. 25, 2013, which is incorporated by reference in its entirety.

SEQUENCE LISTING

The instant application contains a Sequence Listing which has been submitted electronically in ASCII format and is hereby incorporated by reference in its entirety. Said ASCII copy, created on Dec. 4, 2014, is named 14952.0463US_S-L.txt and is 1,399 bytes in size.

TECHNICAL FIELD

This invention relates to a method and apparatus of tracking cell identity.

BACKGROUND

Manipulation and tracking of cells in biological experiments is increasingly important. Most techniques for tracking unique cells utilize complicated methodologies with mixed outcomes.

SUMMARY

A method and apparatus of tracking cell identity across analytical platforms can use stochastic barcoding (SB).

In one aspect, a method of tracking cell identity can include encapsulating a cell in a matrix including a plurality of markers, and imaging the encapsulated cell to create a stochastic barcode corresponding to the single cell.

In certain embodiments, the markers can include polymer beads. The polymer beads can include emissive polymer beads. The polymer beads can be colored. The number of colors can be two to six. The number of colors can be three. The number of colors can be four. The matrix can be a hydrogel.

In certain embodiments, the method can include adding a polymer solution with a plurality of markers into a block of single-cell microwell arrays, encapsulating selected cells and plurality of markers, imaging of arrays to assign a random code based on the plurality of markers, transferring arrays into a microtiter plate, and imaging arrays after transfer to read the code.

The random code can be assigned based on one or more of the number, color, size, and position of markers in the matrix. In certain embodiments, the random code can be assigned based on the number, color, size, and position of markers in the matrix. The encapsulation step can include photopolymerizing or chemical polymerization or thermal polymerization. Assigning a random code can include using a machine learning algorithm. The markers can include polymer beads. The polymer beads can include emissive polymer beads.

In certain embodiments, the polymer beads can be colored. The number of colors can be two, three, four, five, six, seven, eight, nine, ten, eleven, twelve, thirteen, fourteen, fifteen, sixteen, seventeen, eighteen, nineteen or twenty. The number of colors can be two to six. The number of colors can be three. The number of colors can be four. The matrix can be a hydrogel.

In certain embodiments, one hundred cells in an array can be uniquely coded with an average of eight beads per encapsulated cell. An average of fifteen beads per encapsulated cell can yield an approximate 100 percent matching accuracy. An average of fifteen beads per encapsulated cell can yield an approximate 90 percent matching accuracy for one thousand cells.

In another aspect, a composition comprising a hydrogel matrix can contain a biological cell and a plurality of optically visible randomly distributed indicia in the matrix. The indicia can include polymer beads. The indicia can include emissive polymer beads. The polymer beads can be colored. The number of colors can be two to six. The number of colors can be three. The number of colors can be four.

In another aspect, a system for tracking cells can include a well capable of encapsulating a cell unit that includes a plurality of markers, an imager capable of imaging the cell unit that includes a plurality of markers, and an image processor that can correlate an image of the unit cell with a stochastic barcode.

In certain embodiments, the indicia can include polymer beads. The indicia can include emissive polymer beads. The polymer beads can be colored. The number of colors can be two to six. The number of colors can be three. The number of colors can be four.

Throughout the specification, "approximately" or "approximate" means about, substantially or nearly.

Other aspects, embodiments, and features will be apparent from the following description, the drawings, and the claims.

BRIEF DESCRIPTION OF THE DRAWINGS

FIG. 1A shows addition of PEGDA polymer solution with fluorescent beads into microwell array and sealing with glass slide coated with PDMP. FIG. 1B shows encapsulation of all or selected (shown) microwells by photopoylmerization of the hydrogel. Encapsulated beads constitute a random code based on their color, number, and relative positions. FIG. 1C shows removal of glass slide with polymerized blocks and imaging of the blocks to assign the code. FIG. 1D shows resuspension of hydrogel blocks attached to the cover glass slide after uncapping the PDMS microwell array via dissolution of the PDMP sacrificial layer. FIG. 1E shows transfer of resuspended blocks into a tube. FIG. 1F shows transfer of blocks into a microtiter plate by serial dilution. FIG. 1G shows imaging blocks after transfer to read the code. FIG. 1H shows digestion of hydrogel blocks to release encapsulated cells.

FIG. 3A illustrates that images are first processed to contour the blocks and detect beads in the blocks, generating the code. FIG. 3B illustrates that to match the processed block codes, transformations (i.e., XY displacement, rotation and flip) are applied during the image correlation process. FIG. 3C depicts that to perform the correlation, the bead positions are compared between the before\after image codes while applying the transformations in (B) to one of the blocks. (Here, the actual images are shown, but the processing is on the codes). Each pre-transfer block image is compared to all the images from the blocks after transfer, from which the score matrix is generated. Finally, the Hungarian algorithm is used to determine the global set of best image matches and to generate the matching matrix to recover cell identity. FIG. 3D depicts SPB encapsulation and block matching results from complete 100-block experiments. (i-iii) Representative images of blocks during steps B-D of FIG. 1. (iv) Block-matching accuracy from three experiments, with an overall accuracy of 96±2%. The blue framed images show the individual blocks before transfer, and the red framed images show the best candidate predicted by our custom block matching software. Red "X"'s refer to incorrect matches.

FIG. 4A illustrates how stochastic simulations of block matching are implemented to understand how experimental parameters affect matching accuracy. (i) Simulations show that an average number of beads/block k=8 is able to attain ~100% unique codes for 100 blocks. (ii) Simulations can account for bead and block loss during the experiments. For example, matching accuracy decreases if blocks are lost during transfer, but increasing k can restore the accuracy. FIG. 4B depicts simulation of 1000-block matching with k=15 beads/block showing that ~90% accuracy can be attained even with 30% block loss.

FIG. 9 poses the question whether a random approach to barcoding could yield a solution for tracking large cell numbers on the order of $10^3$-$10^4$.

FIG. 23 discloses SEQ ID NOS 1 and 4, respectively, in order of appearance.

FIG. 26A are graphs depicting simulations of the matching accuracy and error (1-accuracy) for N=100 blocks (n=3, no bead loss and no block loss), when using bead color, number, and location (red) or no location (black) in the code. FIG. 26B is a graph depicting simulations (lines, n=5) and experimental results (◇, n=7 experiments) varying block loss and average number of beads per block, k (N=100 blocks). FIG. 26C are graphs depicting simulations of matching accuracy and error for N=10, 100 and 1000 blocks (n=3, bead loss up to 25% of k, bead movement up to 5 µm, and no block loss). FIG. 26D is a graph depicting summary of the scalability of SPB showing the k needed to obtain 0.1% and 1% error in block matching for various N.

FIG. 27A are graphs depicting viability of B16F10 cells following 1 h exposure to indicated concentrations of photoinitiator (up to 1%; left) or 1 h exposure to photoinitiator with 2 min exposure to UV (right). Bars represent average and whiskers represent standard deviation; n=2. FIG. 27B shows capillary electrophoresis and digital gel results for p53 (left) and HPRT (right) following PCR of genomic DNA and RT-PCR of total RNA, respectively, isolated from PEGDA-encapsulated B16F10 cells. Expected amplicon sizes indicated. Lanes: C+, B16F10 cells; S, cell-laden PEGDA blocks; C-, empty PEGDA blocks.

FIG. 28A shows the custom Matlab script for block detection includes: contrast-limited adaptive histogram equalization (adapthisteq function); Top Hat filter (imtophat function); low-pass adaptive noise-removal filter (wiener2 function); conversion of the image to binary image (im2bw function); removal of small objects (bwareaopen function); dilation of detected objects (imdilate function); and filling of found objects (imfill function). FIG. 28B shows the custom Matlab script for bead detection includes four steps: definition of the edge contour from the detected block shape segmentation on the fluorescence channels to identify fluorescent beads; selection of the beads within/on the edge contour of the detected block; definition of a matrix containing information on the detected blocks and associated beads (i.e., location, diameter, color). FIG. 28C shows comparison of bead detection between implemented software and manual counting (N=63 blocks).

FIG. 30A shows Overestimation of beads per block due to residual free-floating beads around the block and attached to the glass substrate. FIG. 30B shows underestimation of the number of beads per block due to a cluster of beads of the same color.

FIG. 31A shows Monte Carlo model for block matching process. A Matlab script was written that implemented the Monte Carlo simulations, including: stochastic generation of codes based on location, color and number of beads; and transformations performed on the generated codes based on effects (i.e., block rotation, block flip, beads loss, beads displacement, block loss) and their experimentally derived mangnitudes. FIG. 31B shows the experimentally observed magnitude distribution of transformations: (i) Comparison of blocks before and after transfer showed a bead loss of 3.1±2.6 (N=48 blocks with k=15.75 beads/block), which led to a 20% bead loss. (ii) Analysis of relative displacement of beads from their original 2D location in the blocks showed a Poisson distribution centered at 2.3±0.2 μm (n=185 beads from N=10 blocks).

FIG. 32A are graphs depicting the influence of bead color is shown: at low numbers of beads per block, the matching accuracy improves when adding extra colors (comparison of one versus three bead colors, black and red curves, respectively). FIG. 32B are graphs depicting bead loss also decreased block matching accuracy, especially at low k values.

FIG. 34A shows microwell array patterned on a glass slide coated with PDMP (well diameter 100 μm, gap of 150 μm) using a photomask (open dots of 100 μm diameter with a gap of 150 μm) and same UV exposure conditions as described in the experimental section, and finally washed with PBS at pH 7.2 to remove exposed areas. FIG. 34B is a graph depicting PDMP layer analysis from the profilometer corresponding to the blue dashed line in A) gave an average thickness of 150 nm.

DETAILED DESCRIPTION

Figure 2:
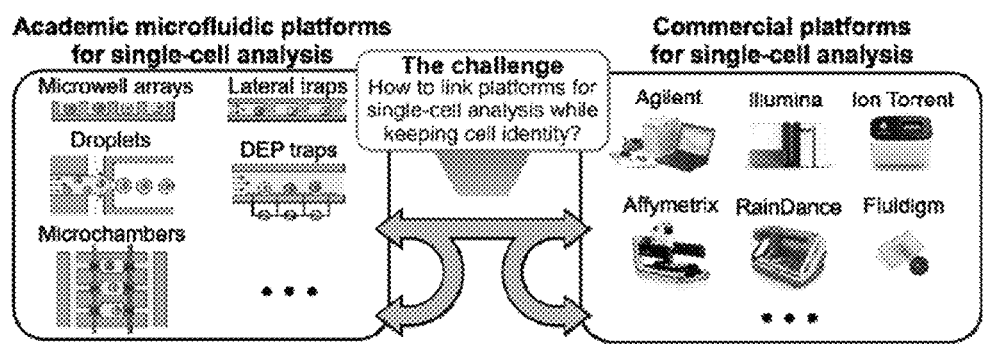
FIG. 2 depicts various types of academic and commercial single-cell analysis platforms.

Acquiring multiparametric data from single cells is critical for assessing phenotype in heterogeneous populations, and is increasingly used across biology. As a result, a diverse set of academic and commercial platforms have been developed to obtain single-cell data (e.g., cytokine secretion, gene expression, function, etc.) (FIG. 2). However, because the academic platforms do not necessarily interface with microtiter plates, transferring cells between platforms while maintaining cell identity is challenging. Here, a simple, scalable method for tracking cell identity across assay platforms is disclosed.

There is an increasing appreciation that understanding biological decision-making requires tracing information flow through cells, which necessitates assaying multiple measures of genotype and phenotype on hundreds or thousands of individual cells. Additionally, there is inherent functional heterogeneity among cell types, among single cells within defined cell types, and even among clonal populations. See, Love, J. C., AIChE Journal 2010, 56 (10), 2496-2502, and Elowitz, M. B.; Levine, A. J.; Siggia, E. D.; Swain, P. S., Science 2002, 297 (5584), 1183-1186, each of which is incorporated by reference in its entirety. This heterogeneity holds significant promise for elucidating the mechanisms of many processes in health and disease and thus motivates the development of assays applicable to sparse populations of cells (defined as single cells or groups of 2-10 cells). See, De Sousa E Melo, F.; Vermeulen, L.; Fessler, E.; Medema, J. P., EMBO Rep 2013, 14 (8), 686-695, Spencer, S. L.; Gaudet, S.; Albeck, J. G.; Burke, J. M.; Sorger, P. K., Nature 2009, 459 (7245), 428-432, Liddiard, K.; Rosas, M.; Davies, L. C.; Jones, S. A.; Taylor, P. R., European Journal of Immunology 2011, 41 (9), 2503-2508, Katayama, H.; Hattori, Y.; Ogata, K.; Yan, H.; Satoh, E.; Teramoto, K.; Arii, S.; Kamide, R.; Nakagawa, H.; Kimura, H., Transplantation Proceedings 2005, 37 (1), 17-19, and Fritzsch, F. S. O.; Dusny, C.; Frick, O.; Schmid, A., Annual Review of Chemical and Biomolecular Engineering 2012, 3 (1), 129-155, each of which is incorporated by reference in its entirety. Novel platforms that have been developed to achieve this goal often center on microfluidic approaches, such as arrays of micro/nano/picoliter-volume wells, microchambers, and emulsion-based droplet technologies. See, Love, J. C.; Ronan, J. L.; Grotenbreg, G. M.; van der Veen, A. G.; Ploegh, H. L., Nature Biotechnology 2006, 24 (6), 703-707, Yoshimoto, N.; Kida, A.; Jie, X.; Kurokawa, M.; Iijima, M.; Niimi, T.; Maturana, A. D.; Nikaido, I.; Ueda, H. R.; Tatematsu, K.; Tanizawa, K.; Kondo, A.; Fujii, I.; Kuroda, S. i., Sci. Rep. 2013, 3, Varadarajan, N.; Kwon, D. S.; Law, K. M.; Ogunniyi, A. O.; Anahtar, M. N.; Richter, J. M.; Walker, B. D.; Love, J. C., Proceedings of the National Academy of Sciences 2012, 109 (10), 3885-3890, Ma, C.; Fan, R.; Ahmad, H.; Shi, Q.; Comin-Anduix, B.; Chodon, T.; Koya, R. C.; Liu, C.-C.; Kwong, G. A.; Radu, C. G.; Ribas, A.; Heath, J. R., Nat Med 2011, 17 (6), 738-743, Wang, J.; Fan, H. C.; Behr, B.; Quake, Stephen R., Cell 2012, 150 (2), 402-412, Fan, H. C.; Wang, J.; Potanina, A.; Quake, S. R., Nature Biotechnology 2010, 29 (1), 51-57, White, A. K.; VanInsberghe, M.; Petriv, O. I.; Hamidi, M.; Sikorski, D.; Marra, M. A.; Piret, J.; Aparicio, S.; Hansen, C. L., Proceedings of the National Academy of Sciences 2011, Brouzes, E.; Medkova, M.; Savenelli, N.; Marran, D.; Twardowski, M.; Hutchison, J. B.; Rothberg, J. M.; Link, D. R.; Perrimon, N.; Samuels, M. L., Proceedings of the National Academy of Sciences 2009, 106 (34), 14195-14200, Leung, K.; Zahn, H.; Leaver, T.; Konwar, K. M.; Hanson, N. W.; Pagé, A. P.; Lo, C.-C.; Chain, P. S.; Hallam, S. J.; Hansen, C. L., Proceedings of the National Academy of Sciences 2012, 109 (20), 7665-7670, and Joensson, H. N.; Andersson Svahn, H., Angewandte Chemie International Edition 2012, 51 (49), 12176-12192, each of which is incorporated by reference in its entirety. Ideally, these novel single-cell assays would be used sequentially with more traditional methods (e.g., single-cell RT-PCR, DNASeq and RNASeq, proteomics) on the same individual cells to more completely link cell signaling, phenotype, and responsiveness.

However, an outstanding challenge for many novel analytical platforms is the ability to retain the identity of individual cells within a population, particularly while transferring them from modern bioanalytical assays such as microfluidic devices to standardized platforms (e.g., microtiter plates) for further analysis. Current solutions to this challenge include cell-by-cell transfer (e.g., capillary-based micromanipulators), fluorescent labeling, barcoding particles (e.g., hydrogel encoded particles, semiconductor tags), or molecular labels. See, Choi, J. H.; Ogunniyi, A. O.; Du, M.; Du, M.; Kretschmann, M.; Eberhardt, J.; Love, J. C., Biotechnology Progress 2010, 26 (3), 888-895, Choi, J. H.; Ogunniyi, A. O.; Du, M.; Du, M.; Kretschmann, M.; Eberhardt, J.; Love, J. C., *Biotechnology Progress* 2010, 26 (3), 888-895, Krutzik, P. O.; Nolan, G. P., *Nat Meth* 2006, 3 (5), 361-368, Perfetto, S. P.; Chattopadhyay, P. K.; Roederer, M., *Nat Rev Immunol* 2004, 4 (8), 648-655, Yamanaka, Y. J.; Szeto, G. L.; Gierahn, T. M.; Forcier, T. L.; Benedict, K. F.; Brefo, M. S. N.; Lauffenburger, D. A.; Irvine, D. J.; Love, J. C., *Analytical Chemistry* 2012, 84 (24), 10531-10536, Dendukuri, D.; Pregibon, D. C.; Collins, J.; Hatton, T. A.; Doyle, P. S., *Nat Mater* 2006, 5 (5), 365-9, Wood, D. K.; Braun, G. B.; Fraikin, J. L.; Swenson, L. J.; Reich, N. O.; Cleland, A. N., *Lab on a Chip* 2007, 7 (4), 469-474, Fernandez-Rosas, E.; Gómez, R.; Ibañez, E.; Barrios, L.; Duch, M.; Esteve, J.; Nogués, C.; Plaza, J. A., *Small* 2009, 5 (21), 2433-2439, Mali, P.; Aach, J.; Lee, J.-H.; Levner, D.; Nip, L.; Church, G. M., *Nat Meth* 2013, 10 (5), 403-406, Oh, B.-K.; Nam, J.-M.; Lee, S. W.; Mirkin, C. A., *Small* 2006, 2 (1), 103-108, and Alon, S.; Vigneault, F.; Eminaga, S.; Christodoulou, D. C.; Seidman, J. G.; Church, G. M.; Eisenberg, E., *Genome Research* 2011, 21 (9), 1506-1511, each of which is incorporated by reference in its entirety. Cell-by-cell manipulation requires direct access to cells and typically has limited throughput due to its serial nature. Fluorescent labeling is successfully used for highly multiplexed detection of bioanalytes, but its application to cell tracking is constrained by the limits of spectral multiplexing and prior knowledge of cell states/labels to generate a labeling scheme to track cells. See, Fournier-Bidoz, S.; Jennings, T. L.; Klostranec, J. M.; Fung, W.; Rhee, A.; Li, D.; Chan, W. C. W., *Angewandte Chemie International Edition* 2008, 47 (30), 5577-5581, and Peck, D.; Crawford, E.; Ross, K.; Stegmaier, K.; Golub, T.; Lamb, J., *Genome Biology* 2006, 7 (7), R61, each of which is incorporated by reference in its entirety. Furthermore, various labeling approaches or dyes may alter cellular function or phenotype. Barcoding particles have struggled with coding depth and/or the challenge of co-localizing the coding particle with the cell, while molecular labels typically destroy the cell during reading, or compromise potential barcode depth in exchange for non-destructive detection (e.g., fluorescence). An ideal method for cell tracking would be 1) scalable for 100's-1000's of cells, 2) selectively able to target a subpopulation based on parameters such as function, 3) non-destructive/non-disruptive to cells to allow multiple assays to be correlated, and 4) allow transfer of cells between arbitrary single-cell or multi-cell assay platforms.

Current methods for tracking identity across assay platforms mainly rely on direct tracking or deterministic codes. Direct tracking by manually picking cells with micromanipulators has disadvantages including limited throughput and requires open access to the cells. See, for example, J. H. Choi, A. O. Odunniyi, M. Du, M. Kretschmann, J. Eberhardt, and J. C. Love, *Biotechnology Progress* 2010, vol. 26, no. 3, pp. 888-895. Deterministic fluorescent labeling is limited by multiplexing depth (i.e., number of colors that can be detected). See, for example, P. O. Krutzik and G. P. Nolan, Nat Meth 2006, no. 5, pp. 361-368 and S. P. Perfetto, P. K. Chattopadhyay and M. Roederer, Nat Rev Immunol. 2004, vol. 4, no. 8, pp. 648-655. Deterministic fluorescent labeling is further limited by the specificity of the label. See, for example, Y. J. Yamanake, G. L. Szeto, T. M. Gierahn, T. L. Forcier, K. F. Benedict, M. S. N. Brefo, D. A. Lauffenburger, D. J. Irvine and J. C. Love, Analytical Chemistry 2012, vol. 84, no. 24, pp. 10531-10536; P. Mali, J. Aach, .H. Lee, D. Levner, L. Nip and G. M. Church, Nat Meth 2013, vol. 10, no. 5, pp. 403-406, each of which is incorporated by reference in its entirety.

Instead, stochastic barcoding (SB), a method that uses bead location and color within a block photo-polymerized around cells to enable high multiplexing depth (1000s of cells) without needing physical access to cells.

The goal of multiparametric single-cell analysis is to understand cell decision-making in immunology, stem cell biology, etc. There is a need for a connected description of molecular events in cells. There is no convenient interface to microtiter plates for many microfluidic devices. Brute force methods exist to keep track of small cell numbers.

As shown in FIG. 2, the types of academic microfluidic platforms for single-cell analysis include microwell arrays, droplets, microchambers, lateral and DEP traps. Commercial platforms for single-cell analysis are used by various companies, including, for example, Agilent, Illumina, Ion Torrent, Affymetrix, RainDance, and Fluidigm.

Current methods for tracking identity across assay platforms mainly rely on direct tracking or deterministic codes. Direct tracking by manually picking cells with micromanipulators has disadvantages including limited throughput and requires open access to the cells. See, for example, J. H. Choi, A. O. Odunniyi, M. Du, M. Kretschmann, J. Eberhardt, and J. C. Love, *Biotechnology Progress* 2010, vol. 26, no. 3, pp. 888-895, incorporated by reference in its entirety. Deterministic fluorescent labeling is limited by multiplexing depth (i.e., number of colors that can be detected). See, for example, P. O. Krutzik and G. P. Nolan, Nat Meth 2006, no. 5, pp. 361-368 and S. P. Perfetto, P. K. Chattopadhyay and M. Roederer, Nat Rev Immunol. 2004, vol. 4, no. 8, pp. 648-655, each of which is incorporated by reference in its entirety. Deterministic fluorescent labeling is further limited by the specificity of the label. See, for example, Y. J. Yamanake, G. L. Szeto, T. M. Gierahn, T. L. Forcier, K. F. Benedict, M. S. N. Brefo, D. A. Lauffenburger, D. J. Irvine and J. C. Love, Analytical Chemistry 2012, vol. 84, no. 24, pp. 10531-10536; P. Mali, J. Aach, .H. Lee, D. Levner, L. Nip and G. M. Church, Nat Meth 2013, vol. 10, no. 5, pp. 403-406; D. C. Pregibon., M. Toner, P. S. Doyle, Science, 2007, vol. 315, 1393-1396; D. K. Wood, G. B. Braun, J. L. Fraikin, L. J. Swenson, N. O. Reich, A. N. Cleland, Lab on a Chip, 2007, vol. 7, 469-474, each of which is incorporated by reference in its entirety.

Instead, stochastic barcoding (SB), a method that uses marker location and color within a block photo-polymerized around cells to enable high multiplexing depth (1000s of encapsulated cell blocks) without needing physical access to cells. A stochastic system is one whose state is non-deterministic so that the subsequent state of the system is determined probabilistically. A cell can be tracked by identifying the number of colored markers around a certain area of the cell, the location of each marker, and the color of each marker. The marker can be any color on the spectrum, for example, blue, red, green, orange, yellow, or purple. The color can be a color visible in an image, including a color due to light absorption or light emission. The number of possible locations of each marker depends on the size of a cell and a matrix where the cell was encapsulated. In one method, the number of marker colors around a cell can be two to six; the number of marker colors around a cell can be three; the number of marker colors around a cell can be four. The number of marker colors around a cell can be one to 16. The number of marker colors around a cell can be one to 20. The number of marker colors around a cell can be more than 20. Therefore, the possibility that a first cell has the same number of markers around it as a second cell, where the markers are at the same location for the first cell and the second cell, and that each marker is the same color for the first cell and the second cell is very low. Accordingly, an image of a cell that captures the number of the markers, the location of the markers, and the color of the markers can serve as a unique identifier for the cell.

The term "marker" can refer to a physical object by which stochastic barcoding may be achieved including, without limitation, colored beads. The marker is an object that can be imaged, but by itself does not carry any identifying information. The marker, such as a bead or other indicium, can include a colored substance, such as an inorganic molecule, an organic molecule, a metal, a nanoparticle, or a combination thereof. The marker can include a polymer, glass, or a dye. The marker can include a dyed microparticle or nanoparticle, a dyed bead, a fluorescent microparticle or nanoparticle. The marker can include a particle that fluorescences under excitation. The size of a marker can be less than 0.1 micron, less than 0.5 microns, less than 2 microns, less than 5 microns, or less than 10 microns. The marker can include negatively charged sulfate groups or positively charged amine groups. The marker can be carboxylate-modified and can be coated with a hydrophilic polymer containing multiple carboxylic acids for covalent attachment of ligands. The marker can include a material with excitation and emission wavelengths that cover the entire spectrum from the near ultraviolet to the near infrared. For example, the color of a marker includes, but not limited to, blue, red, green, orange, yellow, purple, yellow-green, nile red, crimson, dark red, yellow-orange, red-orange, red-purple, blue-purple, blue-green, and yellow-green. The marker can be hydrophobic or hydrophilic. The marker can be carboxylate-modified, can include surface aldehyde group, or can be amine-modified. For example, the marker can include a polystyrene microsphere.

Disclosed herein a method for tracking cells that uses as its code random combinations of beads in a cell-containing hydrogel block; by integrating this method with a previously developed microwell array, we provide the potential to screen cells based on phenotypes or functions (e.g., circulating tumor cells or antibody secretion). The hydrogel blocks comprised a polyethylene glycol diacrylate (PEGDA) photopolymer with an enzymatically cleavable peptide linker. The identity of each block (and its contents) was assigned and tracked using a stochastic barcode generated by the number, color, and position of fluorescently colored beads entrapped in the block matrix. By making the parameter space (number of colors, positions, bead sizes) of the random code sufficiently large, we minimized the probability of two blocks having overlapping codes. This method can be applied to track cells during en masse transfer of cells from arrays of subnanoliter wells (MWA) into microtiter plates. For example, collagenase-mediated digestion of cell-laden blocks enables non-destructive recovery of viable tracked cells and successful nucleic acid isolation and assays. Monte Carlo simulations can be used to assess the scalability of this method up to 1000's of uniquely coded blocks with arbitrary accuracy. This method now enables tracking of sparse populations of cells across platforms and utilizing previous processes developed for the microwell array platform, enabling the potential connection of genotype, phenotype, and function.

Overview of Stochastic Particle Barcoding (SPB)

In tracking sparse populations across platforms, a method that had high coding depth (up to 1000's of unique codes) can be used that would not require physical access to the cells as required by pre-generated barcodes (e.g., fluorescent dyes), but rather allowed codes to be built onto the cells in situ, and that could be used with diverse bioanalytical platforms. The main concept underlying stochastic particle barcoding (SPB) is a code that is randomly built around the cells via an in situ polymerization step. This code is determined by the number, fluorescent color, and position of beads photopolymerized around a set of cells, which allows identity tracking of cells across analytical platforms.

Figure 1:
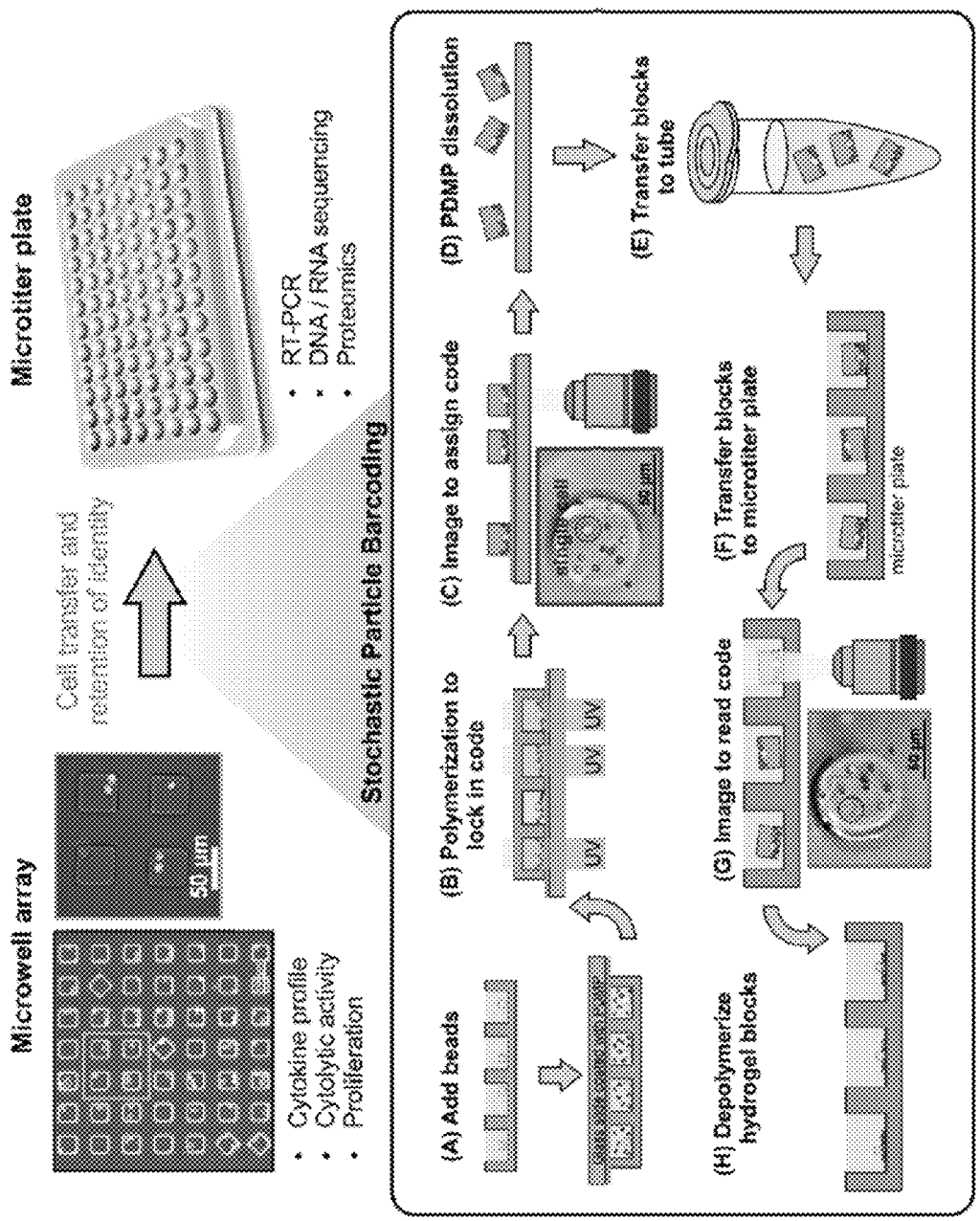
FIG. 1 schematically depicts a method of stochastic barcoding using a randomly generated code determined by the number, color, and position of beads added to and polymerized in a hydrogel block around a set of cells.

This method can be implemented within a novel platform (MWA) that enables dynamic interrogation of cell function where subsequent transfer of cells to a microtiter plate is useful for integrative analysis (FIG. 1). In this workflow, an initial assay on individual cells is carried out in the MWA (an example analysis is discussed further below). Once this initial assay is performed, a prepolymer solution (poly (ethylene glycol) diacrylate (PEGDA) or a digestible acrylate-PEG-peptide-PEG-acrylate, macromonomers commonly used for cell encapsulation in tissue engineering; see, Lee, S.-H.; Miller, J. S.; Moon, J. J.; West, J. L., *Biotechnology Progress* 2005, 21 (6), 1736-1741, which is incorporated by reference in its entirety), containing a suspension of beads of different fluorescent colors (red, green and blue) is pipetted onto the MWA (FIG. 1A). The device is sealed with a glass slide that is coated with a pH-sensitive sacrificial layer, poly(2,2-dimethoxy nitrobenzyl methacrylate-r-methyl methacrylate-r-poly(ethylene glycol) methacrylate) (PDMP). See, Doh, J.; Irvine, D. J., *Journal of the American Chemical Society* 2004, 126 (30), 9170-9171, Katz, J. S.; Doh, J.; Irvine, D. J., *Langmuir* 2005, 22 (1), 353-359, and Kim, M.; Choi, J.-C.; Jung, H.-R.; Katz, J. S.; Kim, M.-G.; Doh, J., *Langmuir* 2010, 26 (14), 12112-12118, each of which is incorporated by reference in its entirety. Sealing enables the generation of discrete hydrogel blocks. Then, the device is flipped to allow the beads to settle; sedimentation of the beads onto the plane of the wells in contact with the sealing glass slide simplifies subsequent imaging-based identification and image processing steps. Next, either the entire array or individual microwells is photopolymerized to lock in the codes, comprising the random distributions of number, fluorescent color, and 2D location of the beads at the boundary of the microwells with the glass slide (FIG. 1B). Once the code was locked, the glass slide is removed from the MWA and imaged the cell-encapsulating hydrogel blocks (FIG. 1C). This step yielded the first set of images, from which a code was assigned to each block corresponding to known positions in the MWA. The PDMP sacrificial layer was then detached to detach the blocks (FIG. 1D) and transferred into eppendorf tubes (FIG. 1E). The blocks were finally transferred into a microtiter plate by serial dilution (FIG. 1F) to obtain a single hydrogel block per well. Then, the blocks were imaged again to read the code and this second set of images was used to match blocks in the microtiter plate with those from the MWA, identifying individual cells from the original assay (FIG. 1G). Finally, the hydrogel blocks can be degraded by adding an enzyme, such as collagenase, to recover encapsulated cells for further analysis (FIG. 1H).

FIG. 1A schematically depicts a method of stochastic barcoding using a randomly generated code determined by the number, color, and position of beads added to and polymerized in a hydrogel block around a set of cells. Because these three parameters are used, high coding depth is achieved using a modest number of beads, with little likelihood of overlapping codes. A simple and scalable code with maximized code depth and minimized imaging complexity may be accomplished by bead number, bead color and bead location. Specifically, the code is stored as a matrix of these three variables. An example follows:

Bead [1] position (x,y), bead [1]1 color, . . . .
Bead [2] position (x,y), bead [2] color, . . . .
Bead [n] position (x,y), bead [n] color.

A theoretical coding depth of three beads (for example, red, green, and blue colors) with 50 discernible positions for each bead yields approximately $50^3$, which is approximately $10^5$ codes. Thus, the bead number, color, and position provide a simple, yet deep, code.

For cell and code encapsulation, a polymer solution is prepared consisting of 20% PEGDA (MW1000) and 1% Irgacure 2959 as photo-initiator, to obtain fast polymerization. A simple UV direct-writing approach through a microscope objective is used to photopolymerize the regions of interest. See, for example, U.S. Patent Application Ser. No. 20100092393 A1, which is incorporated by reference in its entirety.

Imaging of the hydrogel blocks after photopolymerization assigns the code to the cell, and imaging after transfer to the recipient container reads the code. A custom Matlab script was implemented to identify the codes from the images and find the best candidate to match images of pre- and post-transferred blocks. Finally, a model for the stochastic barcoding method was developed.

Block Matching

Figures 3A, 3B, 3C:
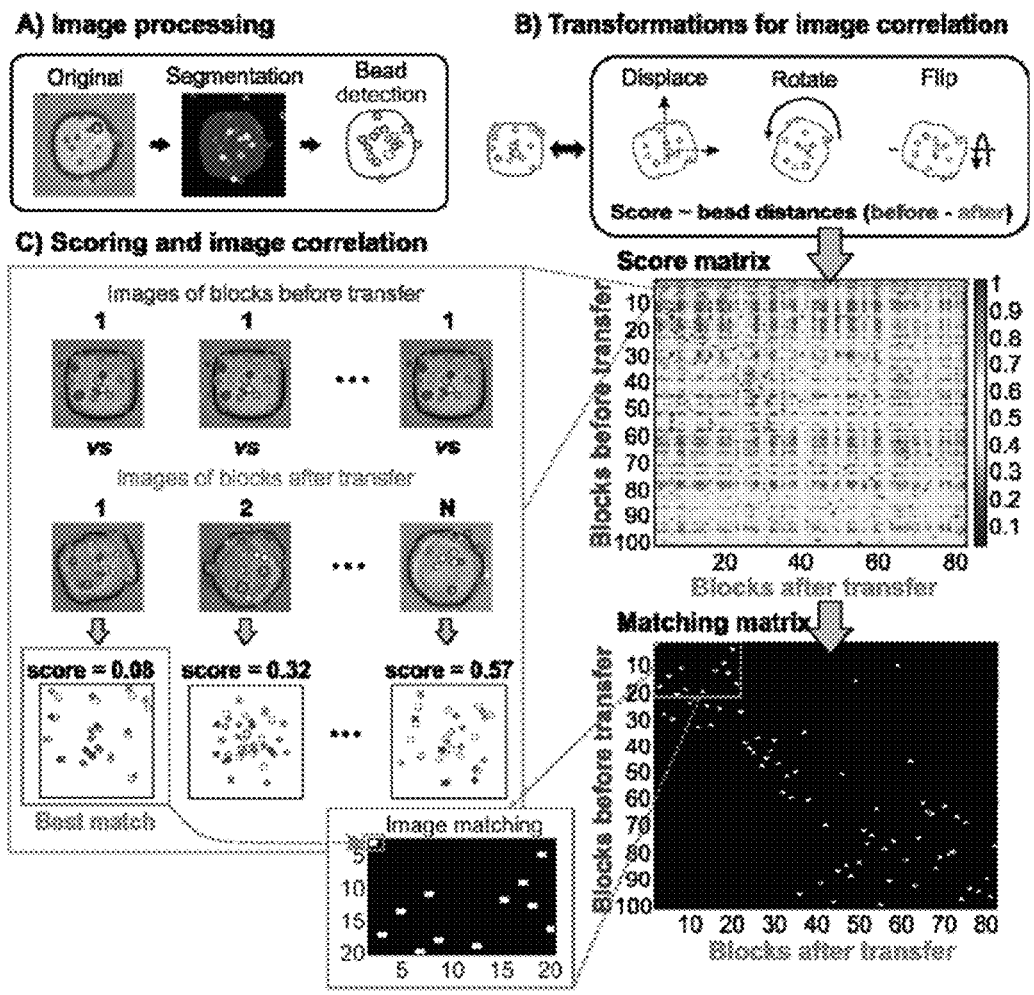
FIGS. 3A-3D depict code matching, which requires correlating images of blocks prior to transfer with those after transfer.
Figure 28A:
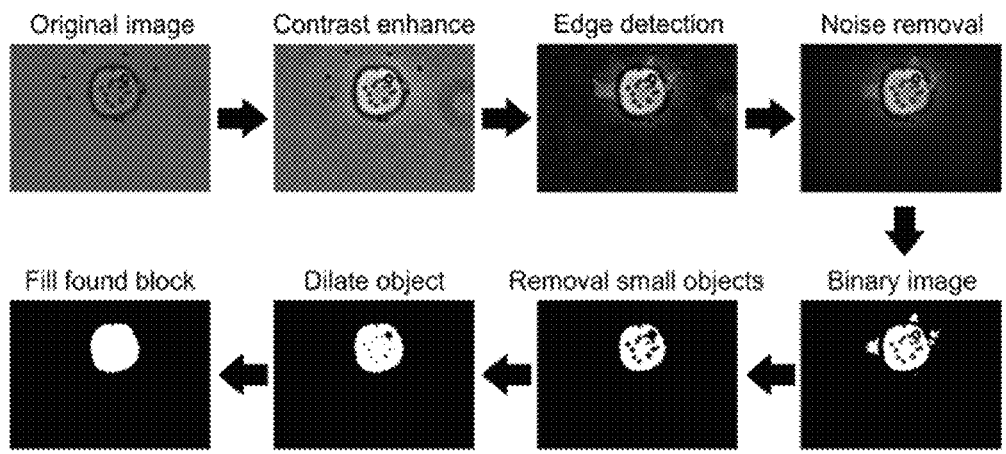
FIG. 28A-28C depict image processing workflow for detection of blocks and beads.
Figure 28B:
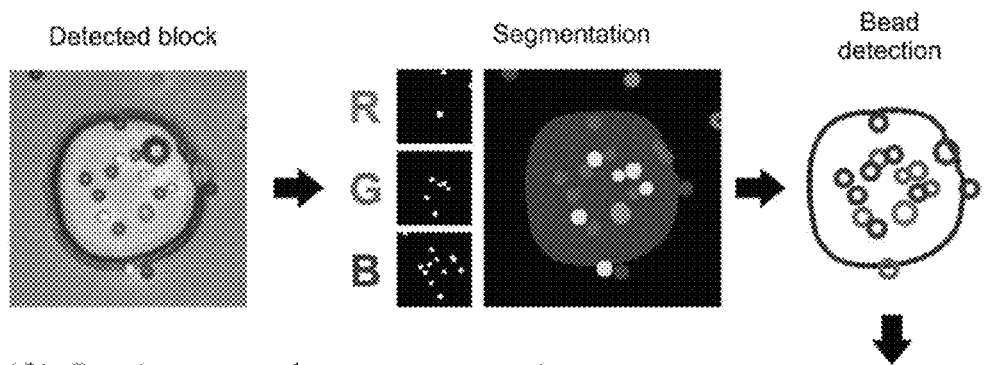
Figure 28C:
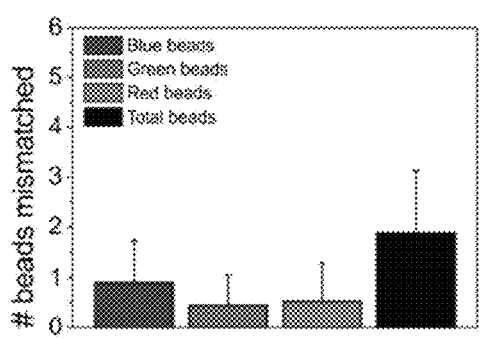

Block identity can be recovered by matching two sets of block images: one taken after photopolymerization and one after plate transfer. Instead of performing computations on the block images themselves, extracted the code information (bead number, color, and position) was extracted and computations were performed on the reduced data set. The images were first segmented to find the outline of each block and the associated beads, recording their color and 2D position (FIGS. 3A and 28). For matching blocks, beads detected inside or on the block perimeter were considered; the position and color of each bead was stored in a matrix for every block.

The matrices associated with each block were compared from the first and second set of images and a global optimization was performed to obtain the best set of matches. Each block from the first set of images was compared to each block from the images after transfer by applying different transformations (translation, rotation, and flipping) to computationally identify the best overlap of the beads in the two blocks (FIG. 3B). Each comparison of these transformations was scored via a measure of the bead distances between the two blocks, adding a penalty for missing or extra beads, and then recording the minimal score (FIG. 3C). A score matrix was generated by finding the minimal scores for each block comparison. A global optimization was then applied to this score matrix (Hungarian algorithm script from Matlab) to obtain a matching matrix that contained the best estimates for block matching, thus recovering block identity (FIG. 3C).

To assess the overall accuracy of the block-matching process, sets of 100 blocks containing B16F10 cells were created, transferred them from a microwell array (MWA) to microtiter plates, and matches were compared via the imaging algorithm versus ground-truth manual scoring. From the MWA, we first selectively photopolymerized wells containing cells of interest (FIG. 3D(i)). Direct UV writing with a fully motorized microscope was used to selectively photopolymerize microwells; this hardware had sufficient throughput for selecting 100's of single cells. To increase throughput even further, it should be possible to employ micromirror arrays (DMDs; see, Zhang, A. P.; Qu, X.; Soman, P.; Hribar, K. C.; Lee, J. W.; Chen, S.; He, S., *Advanced Materials* 2012, 24 (31), 4266-4270, which is incorporated by reference in its entirety) to selectively photopolymerize a large number of selected microwells en masse. We also note that photopolymerization is not restricted to microwells; any shape and even isolated sets of cells can be encapsulated in photopolymer blocks.

Figure 3D:
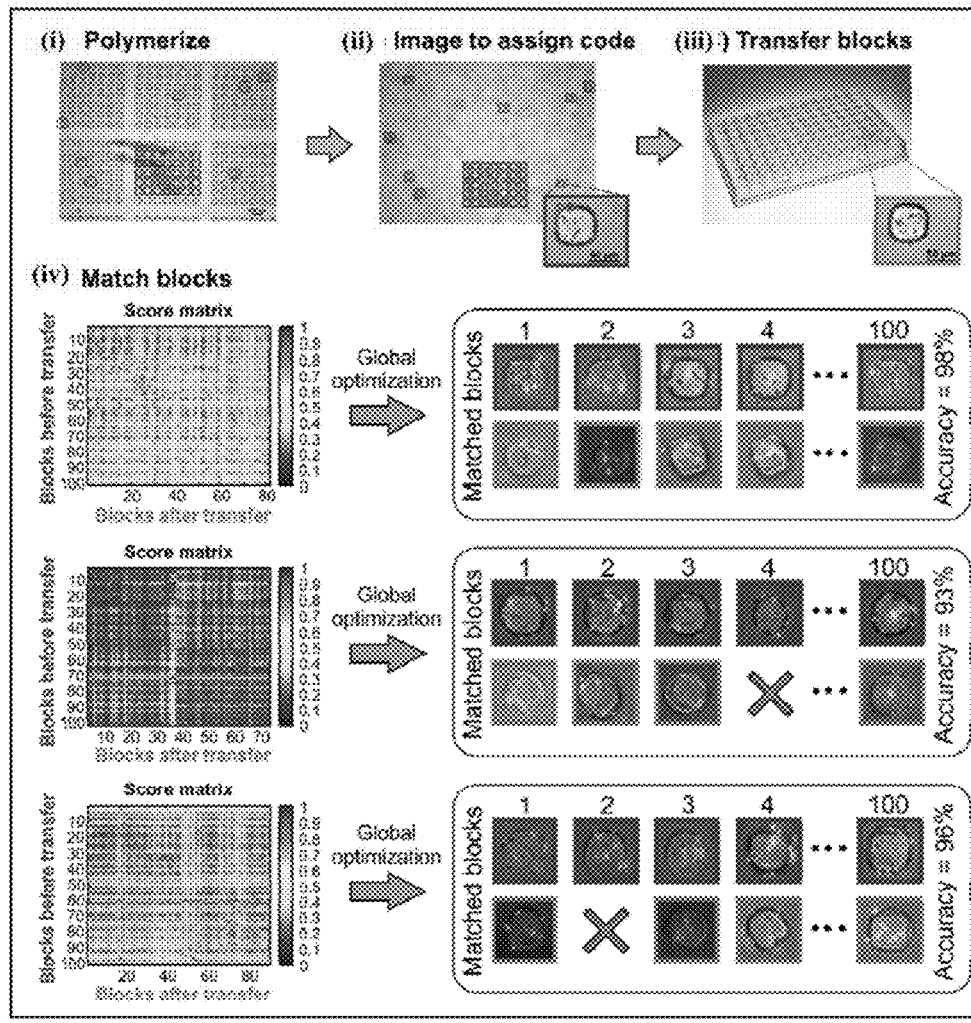
Figure 29:
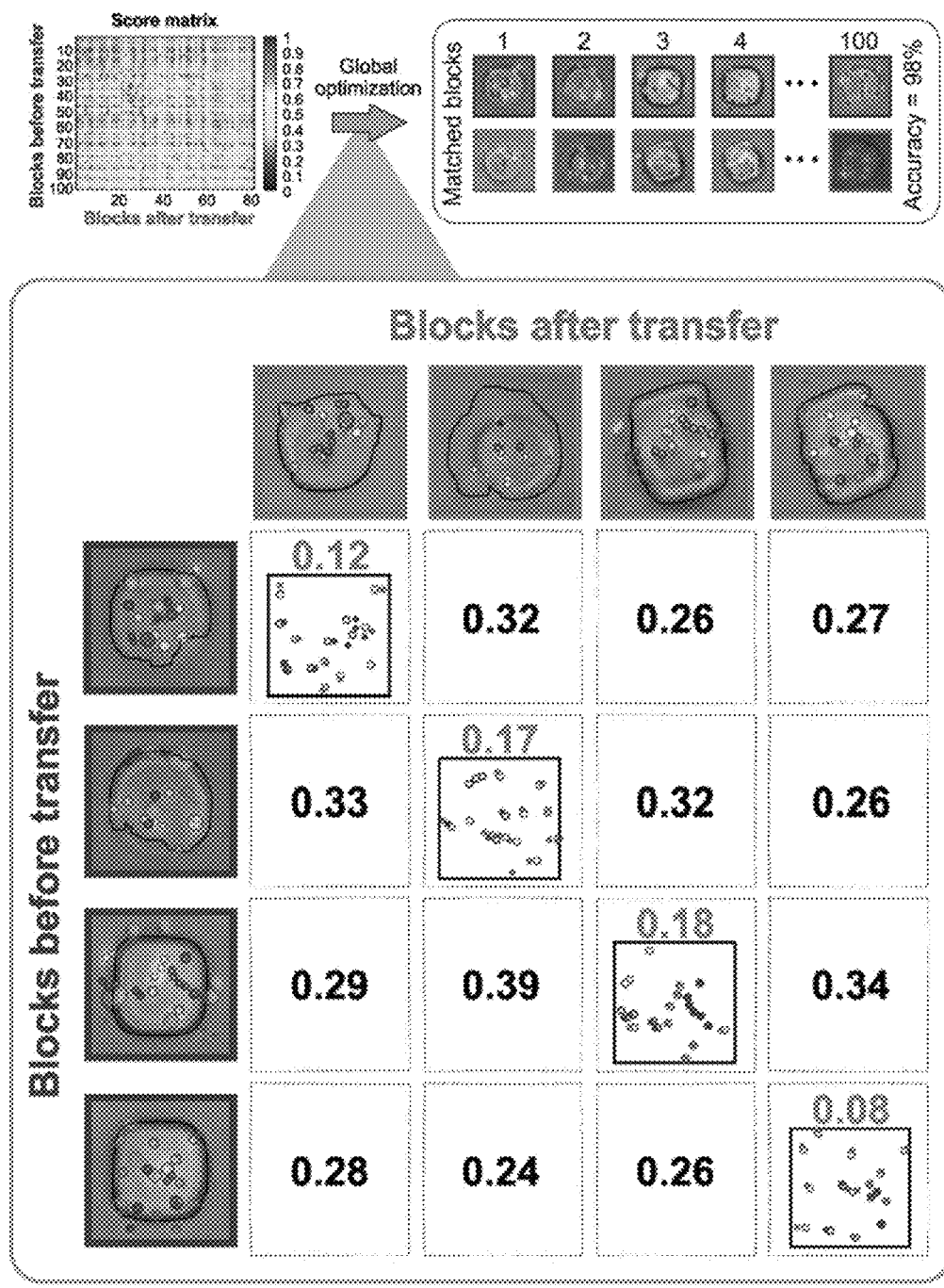
FIG. 29 depicts block matching. Subset of polymer blocks images (before and after transfer step) showing block and beads detention (after image processing step), block comparisons scores, and best matching (scores in green).
Figure 30A:
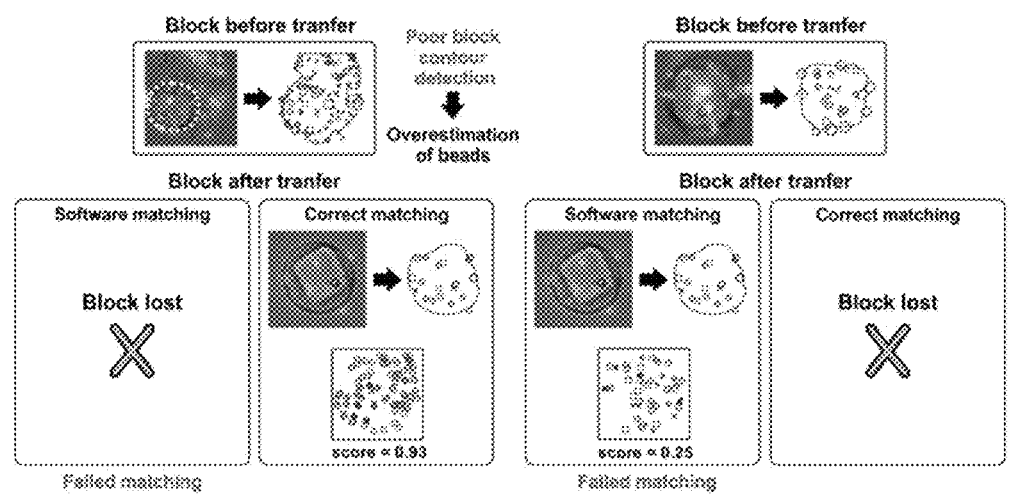
FIGS. 30A-30B depict sources of errors in the block matching process.
Figure 30B:
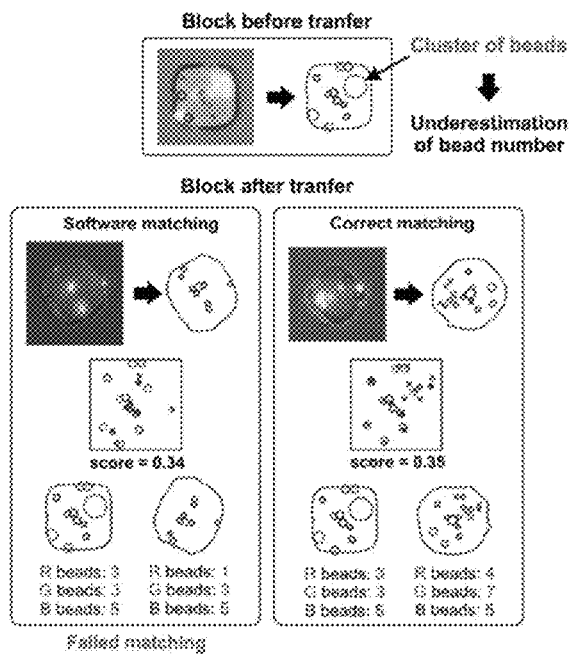

When removing the glass slide from the MWA, only the contents of the selected wells were transferred to the cover glass slide (FIG. 3D(ii)); the hydrogel blocks were imaged to assign a code to each block. The individual blocks were imaged again after transfer to a microtiter plate (FIG. 3D(iii)). FIG. 3D(iv) shows three sets of experiments using a bead concentration that yielded an average of 15 beads per block. Images of individual blocks were processed to determine bead information (i.e., location and color) for block comparison. FIG. 29 demonstrates the block matching process, showing a subset of blocks and the associated matching scores. In the block matching matrix, detected beads in blocks after transfer, detected beads are represented with balls of the same color than the bead. Comparing the computational analysis with manual inspection, the block-matching accuracy of this process for individual experiments on 100 blocks ranged from 93-98%, with an average accuracy of 96%. By manual image inspection of the matching errors, we identified two main sources of error during the identification process (FIGS. 30A-30B): (1) Residual free-floating beads that can attach to the glass substrate near blocks and are mistakenly identified as part of that block (FIG. 1C), leading to an overestimation of the number of beads per block. FIG. 30A shows an example where the software considered the block to be lost during the transfer process because of the large discrepancy in the number of beads detected for the correct block before and after transfer. This discrepancy led to a normalized score for the comparison with the correct block close to 1, where a high score indicates a low probability of correct matching. However, the software assigned this block identity after transfer to another initial block that was actually lost during the transfer process. Washing mitigates this source of error, and it is conceivable that alternative surface functionalization of the beads could reduce this even further. (2) Bead clusters are sometimes mistakenly segmented into single large beads during image processing, which can be addressed with more sophisticated segmentation or heuristics. FIG. 30B demonstrates underestimation of the number of beads per block due to a cluster of beads of the same color. Even though the block correspondence before and after the transfer process is visually clear, the discrepancy in the number of beads led the software to assign the identity of an incorrect block with a similar number of beads in each color. Overall, the results demonstrate that the approach for random coding is feasible and can attain useful accuracy.

The total time for photopolymerization, initial barcode imaging, transfer to the second assay, and re-imaging of blocks averaged ~3 hrs per 100 blocks. The most time-consuming steps in the SPB process are the imaging steps (FIGS. 1C and 1G) and the code matching process. However, imaging throughput could be increased by optimizing the imaging steps (i.e., magnification, numerical aperture, and camera resolution to maximize the number of blocks imaged/time). Additionally, since matching can be performed offline after the experiment is completed, its throughput needs are secondary.

FIG. 3A depicts code matching, which requires correlating images of blocks prior to transfer with those after transfer (FIGS. 3A-3D). First, the block images are processed to determine the contour of the blocks, so then the number, color, and location of the beads within each block can be identified, thereby assigning the code (FIG. 3A). To match the post-transfer images to the pre-transfer images, the fact that blocks can rotate, flip, lose beads, and lose blocks is accounted for (FIG. 3B). The positions for all beads/block between the two sets of images is also accounted for to determine a score that is minimized for the best-matching blocks, and then global optimization using a Hungarian optimization algorithm determines the overall set of best matches (FIG. 3C). Implementing this method to select subpopulations of 100 blocks, an average identification accuracy of 96% is obtained (FIG. 3D) when using an average of 15 beads/block (k).

Figure 4:
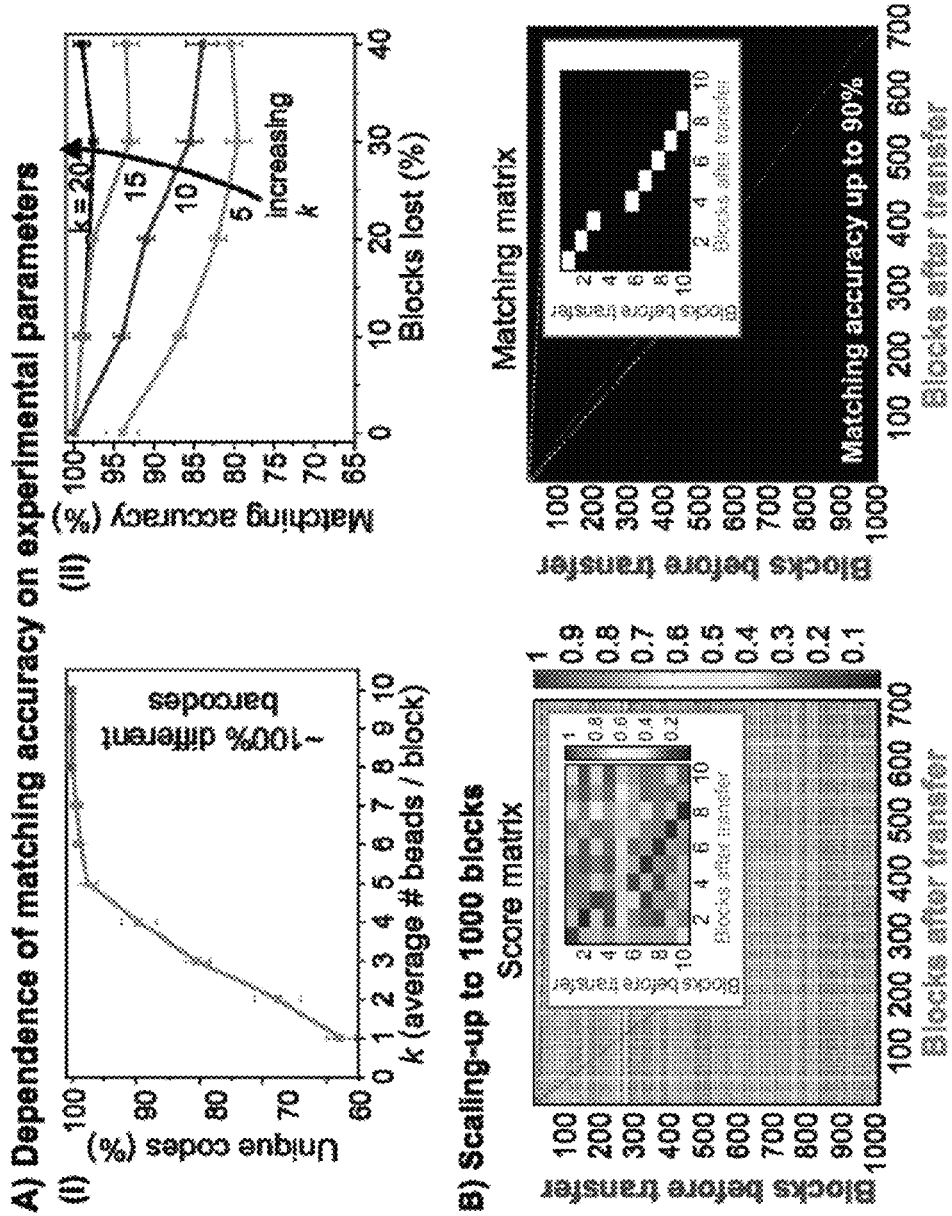
FIG. 4 depicts accuracies achieved using stochastic modeling for up to 1000 blocks and varying numbers of beads.
Figure 5:
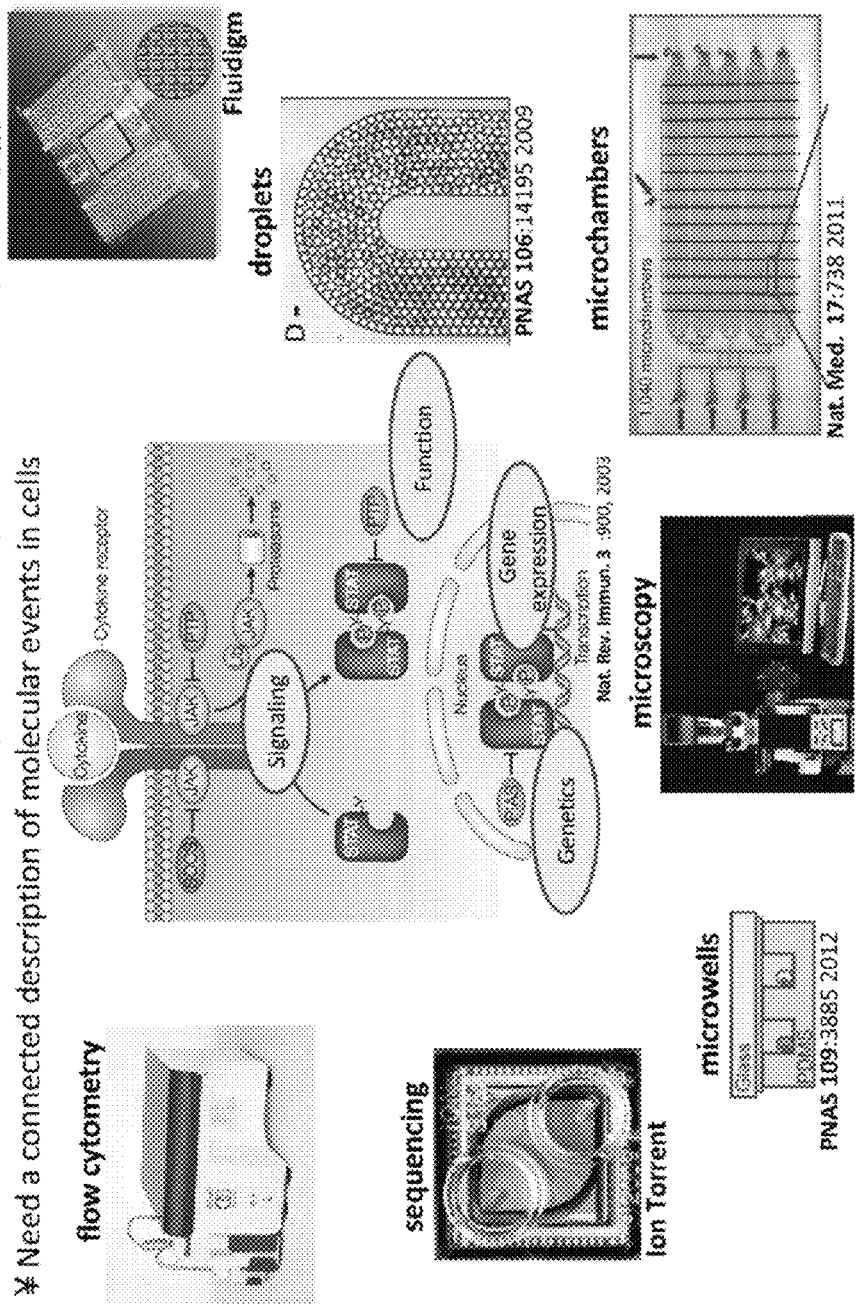
FIG. 5 depicts various types of multiparametric single-cell analyses.
Figure 6:
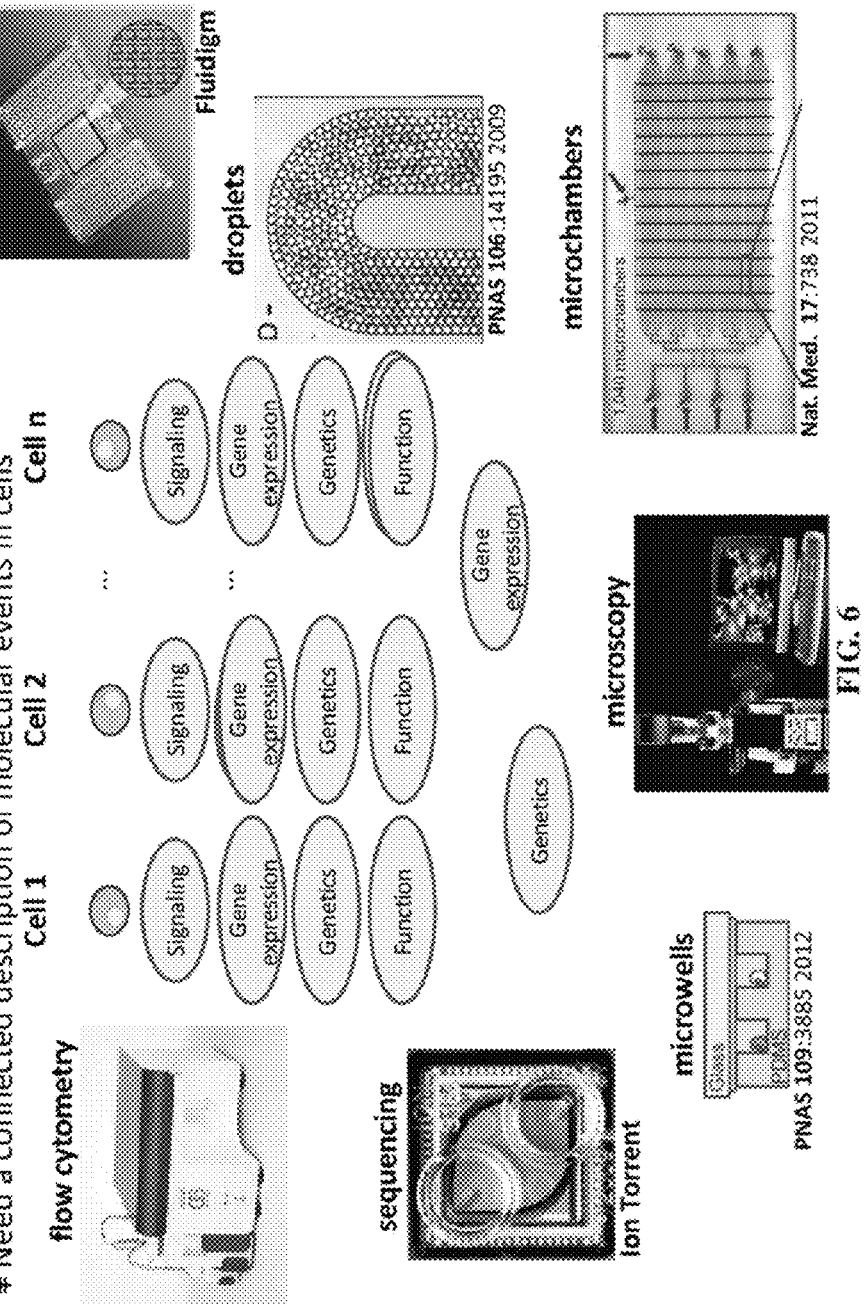
FIG. 6 depicts sequencing of single cells in the multiparametric context.
Figure 7:
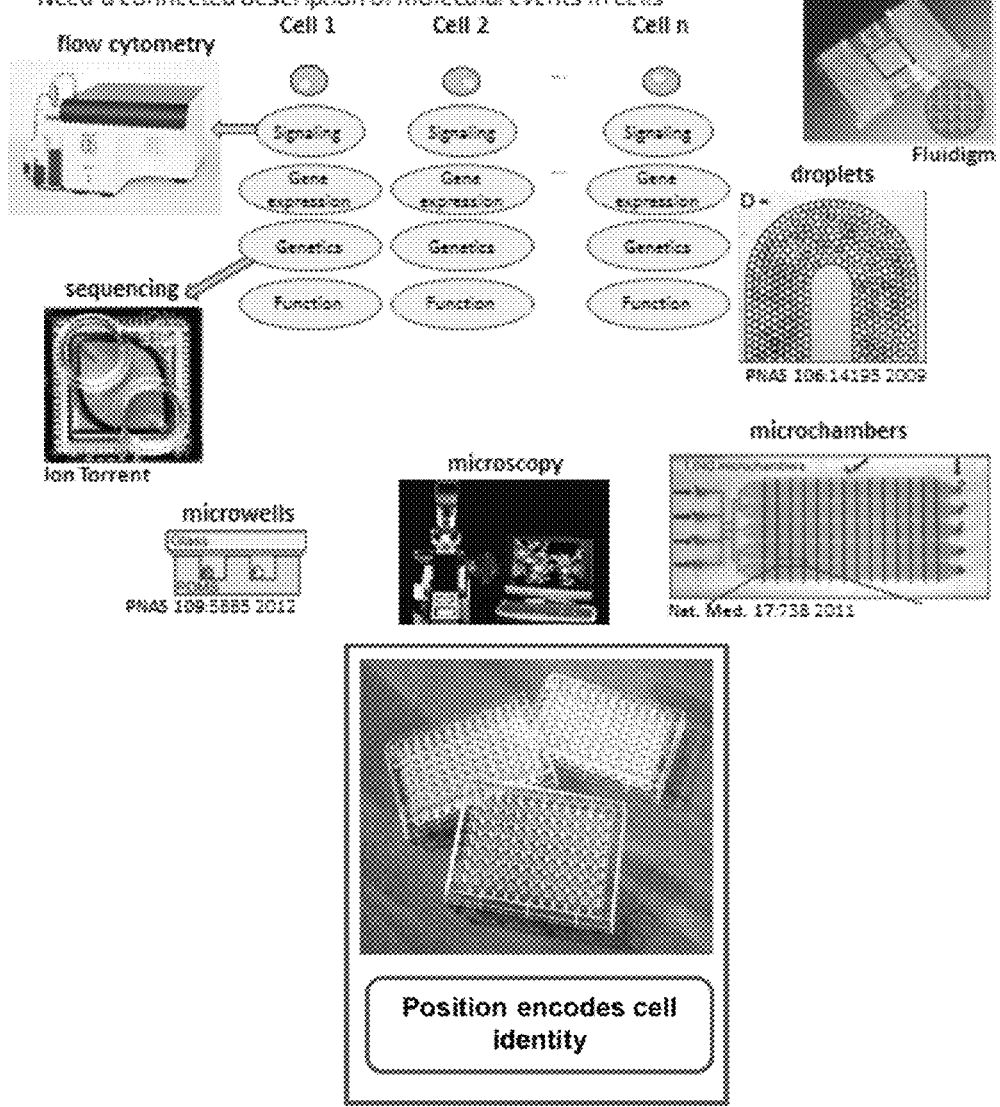
FIG. 7 illustrates that position within an array encodes cell identity.
Figure 8:
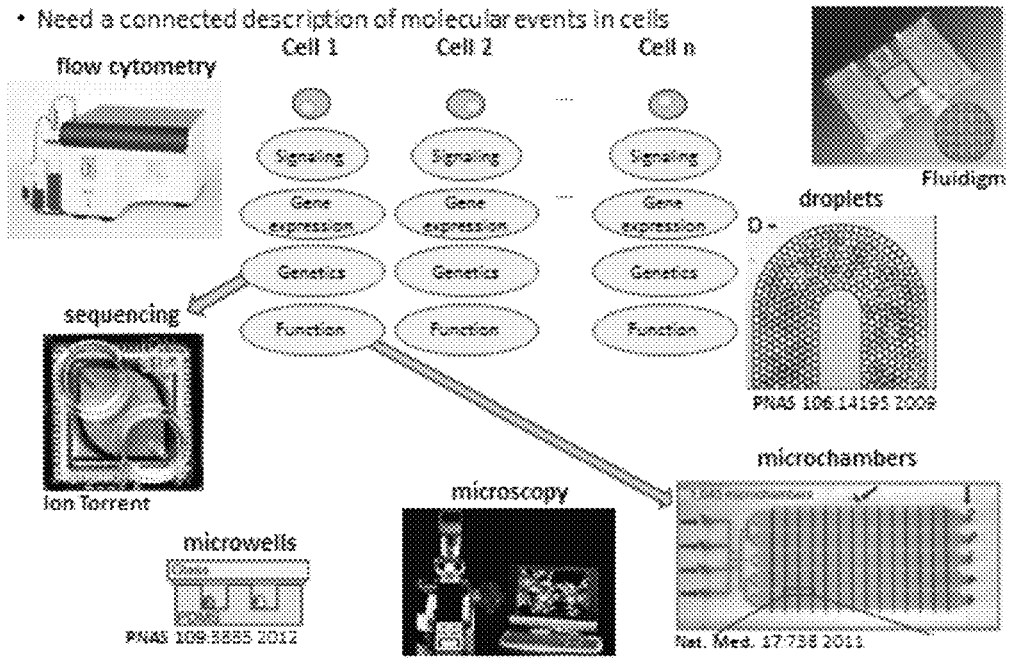
FIG. 8 identifies a lack of convenient interface between microtiter plates and microfluidic devices.
Figure 9:
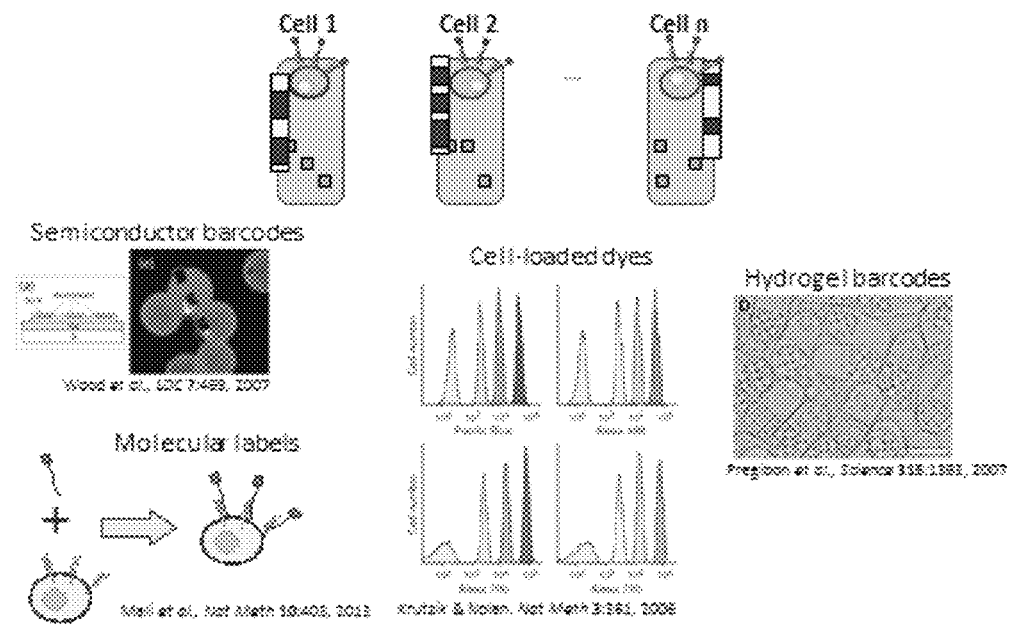
FIG. 9 depicts current cell barcoding deterministic approaches, including semiconductor barcodes, hydrogel barcodes, cell-loaded dyes, and molecular markers.
Figure 10:
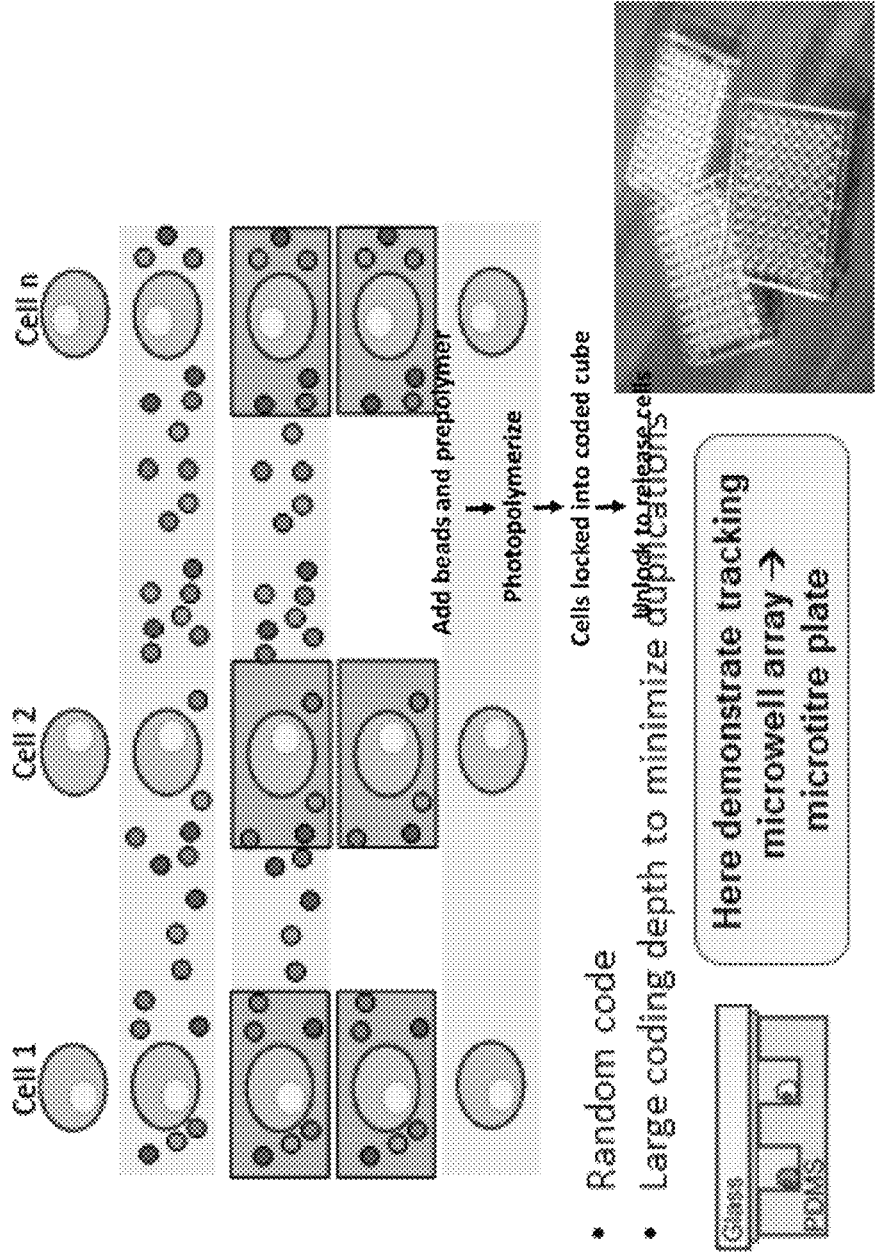
FIG. 10 depicts an experimental approach to testing random code using M&M's and ice cubes to simulate cell tracking between microwell arrays and microtiter plates.
Figure 11:
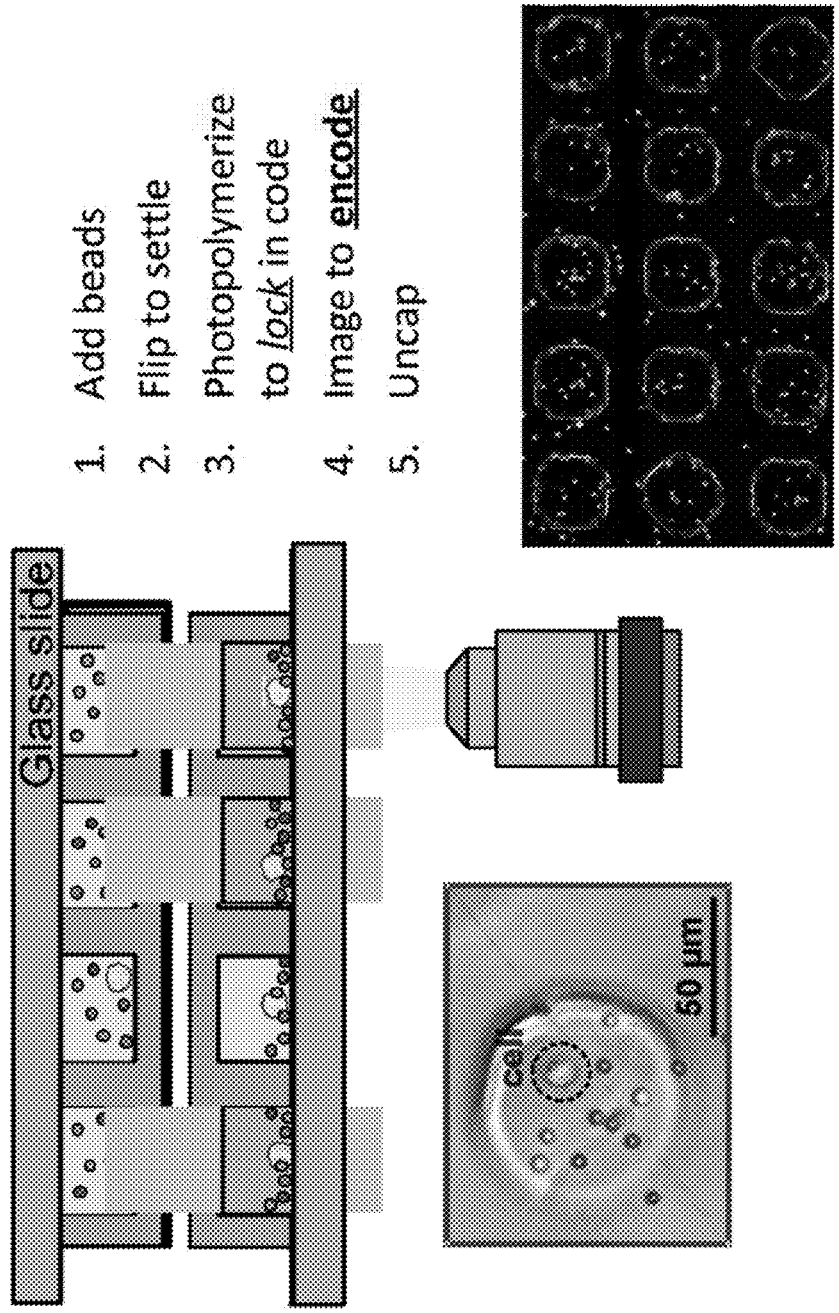
FIG. 11 further depicts a stochastic barcoding approach using the following steps of 1. Adding beads; 2. Flipping to settle; 3. Photopolymerize to lock in code; 4. Imaging to encode; and 5. Uncapping the photopolymerized cell blocks.
Figure 12:
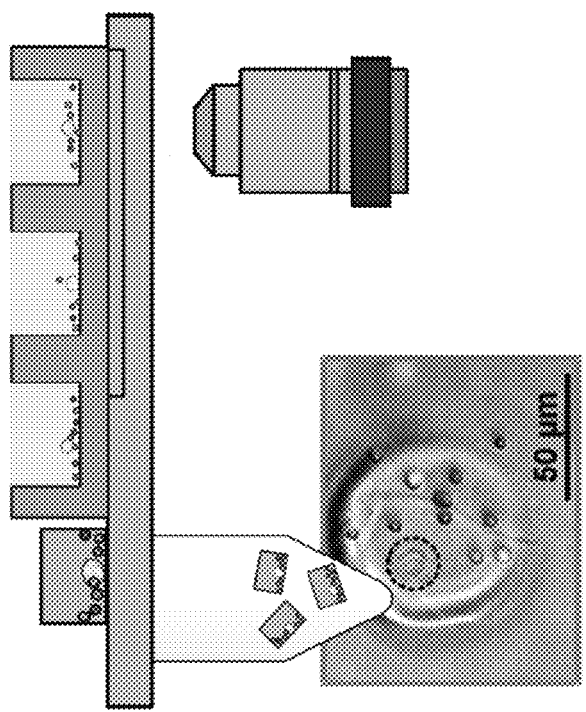
FIG. 12 builds on the stochastic barcoding approach of FIG. 11 by adding the following steps: 6. Transferring the photopolymerized cell blocks to a tube; 7. Transferring the tube to a microtiter plate; 8. Imaging to decode; and 9. Depolymerizing the blocks to access the cells.
Figure 13:
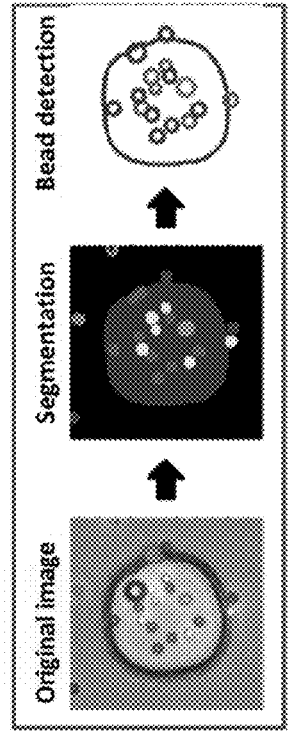
FIG. 13 illustrates the process for setting the code in the stochastic barcoding approach.
Figure 14:
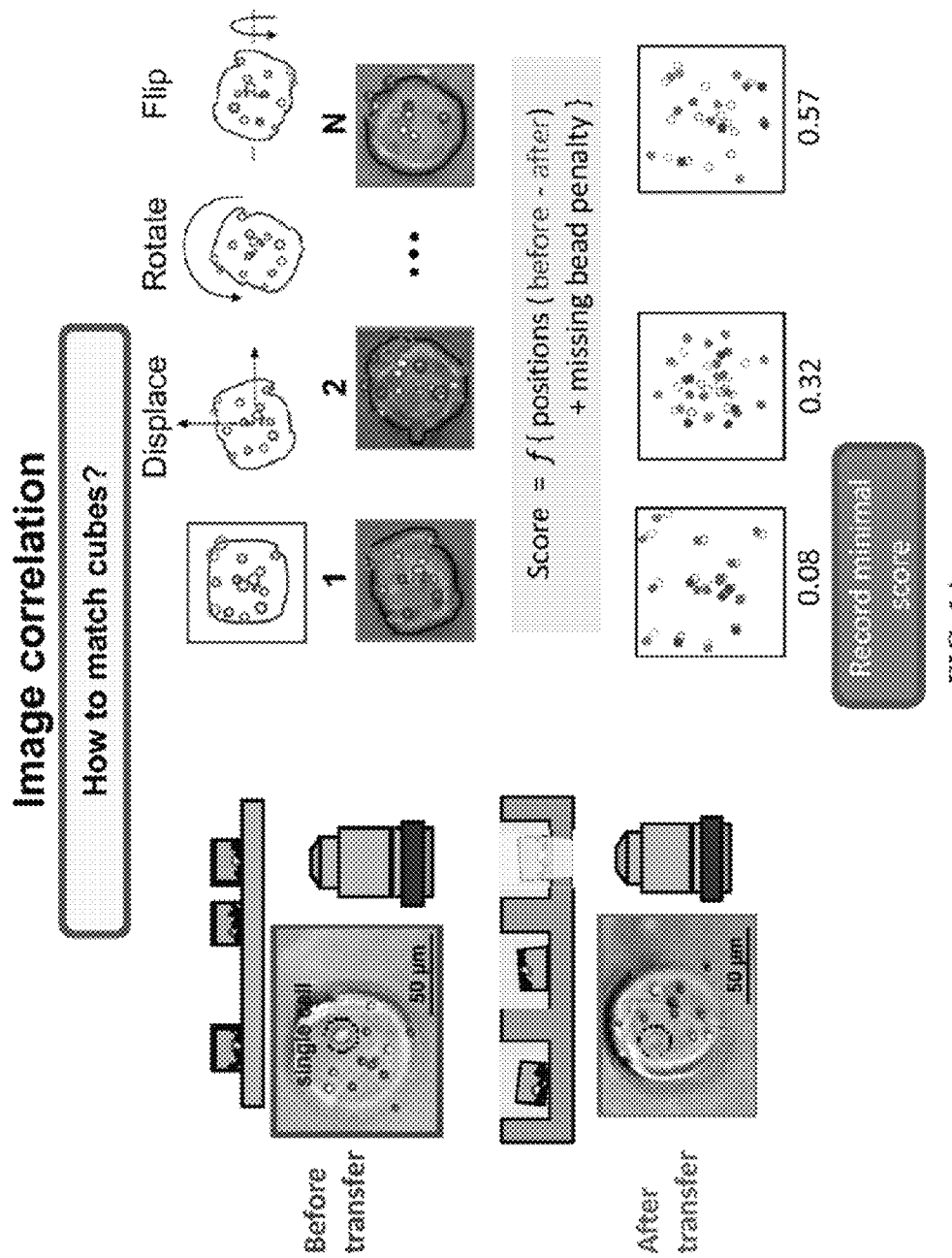
FIG. 14 depicts image correlation before and after transfer the cell blocks, taking into account that the polymer cell blocks can be displaced, rotated, or flipped. A minimal score of positions before − after + missing bead penalty is recorded.
Figure 15:
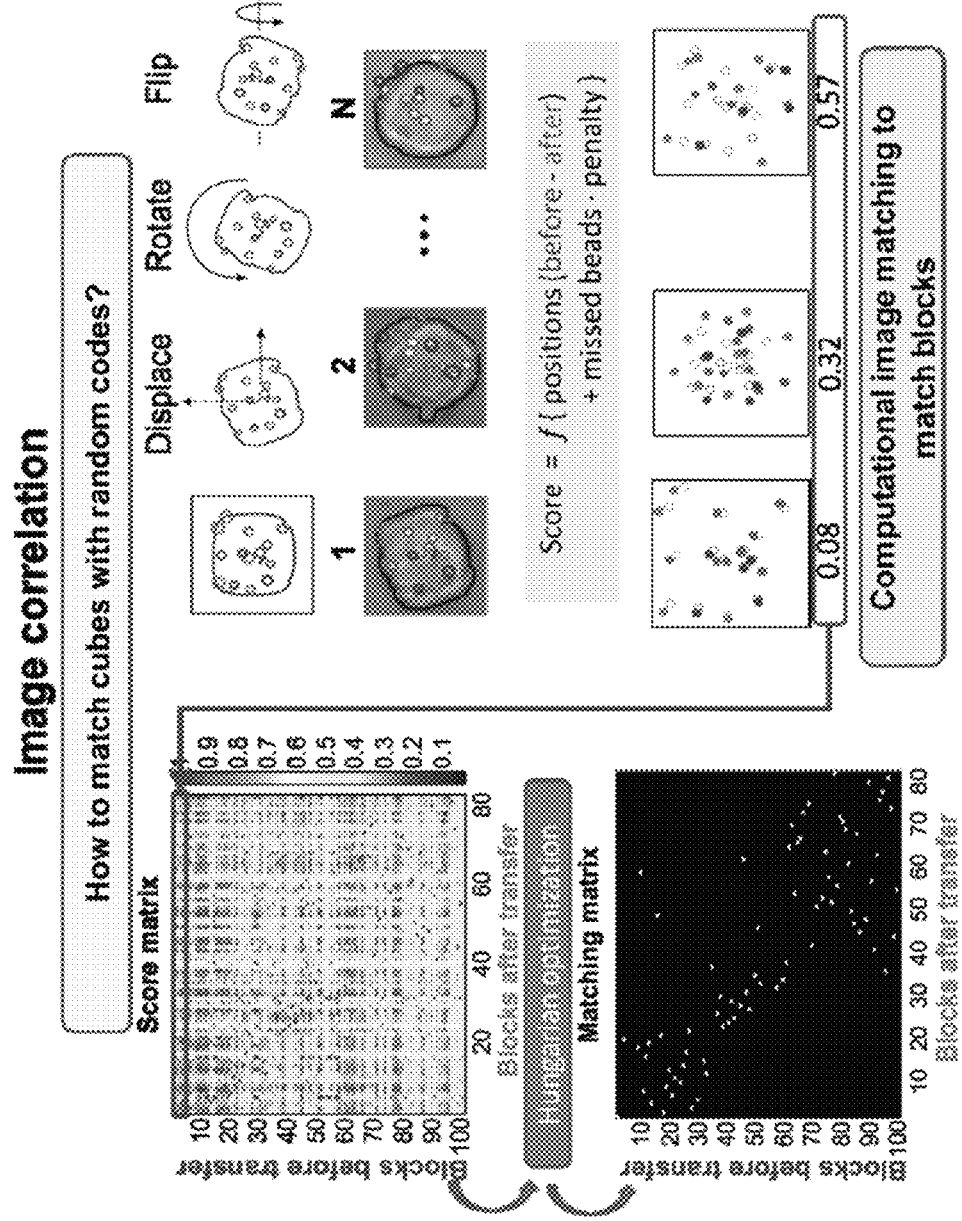
FIG. 15 illustrates using a Hungarian optimization algorithm to provide computational image matching to match blocks.
Figure 16:
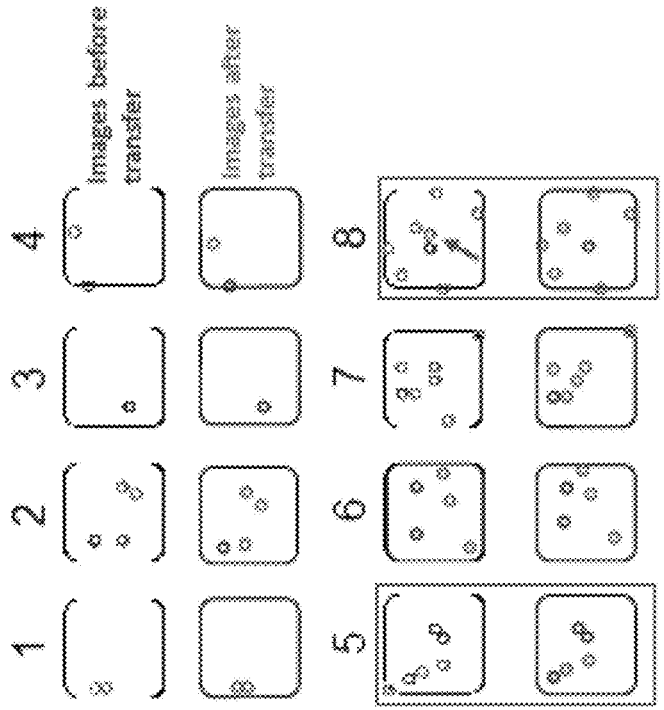
FIG. 16 depicts modeling the stochastic barcoding process using a Monte Carlo matching model.

This is consistent with stochastic modeling, which shows that ~100 blocks can be uniquely coded with k=8 beads/block, and that k=15 beads/block is able to achieve ~100% matching accuracy while tolerating up to 20% block loss (FIG. 4A). Finally, scaling of the method up to 1000 blocks was modeled, and found that k=15 beads/block is able to achieve ~90% accuracy (FIG. 4B). Scaling to even larger numbers of blocks merely requires increasing the number of beads/block, and thus SB provides a simple, scalable approach to maintaining identity of cells across platforms.

This process was modeled using a Monte Carlo model of matching process by computationally generating different numbers of blocks with probabilistic distributions of numerous variables including bead number (k), bead color, bead locations, bead loss between two sets of images, block loss between two sets of images, and bead movement between two sets of images. These probabilistic distributions were informed by experimental data.

Figure 17:
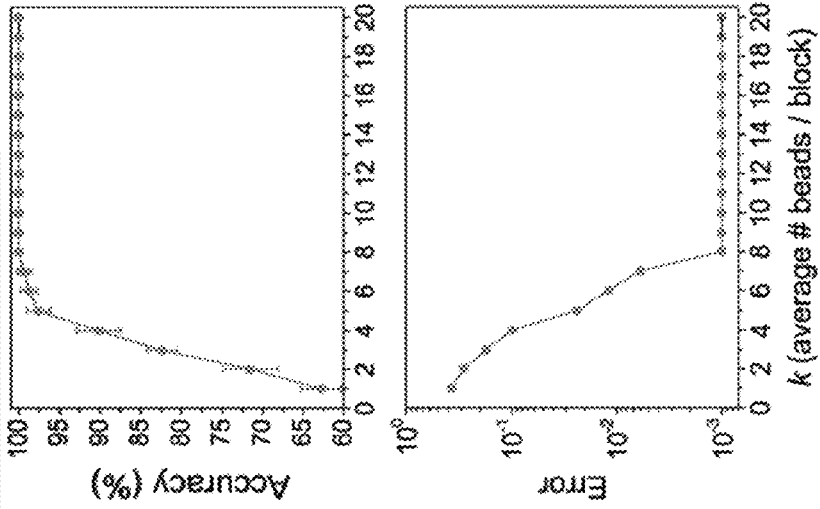
FIGS. 17-19 depict the accuracy of the modeled stochastic barcoding process as a function of the number of beads and the number of beads lost during transfer and conclude that the accuracy can be increased by either increasing the number of beads or minimizing the number of beads lost.
Figure 18:
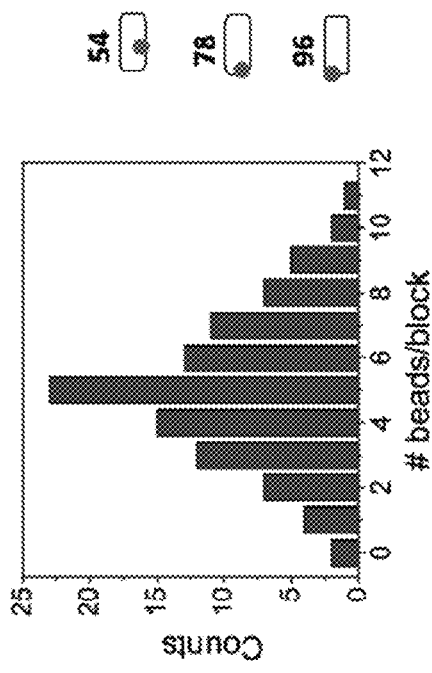
Figure 19:
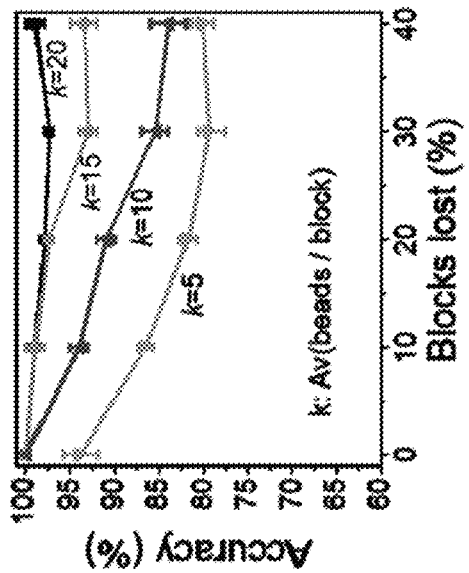
Figure 20:
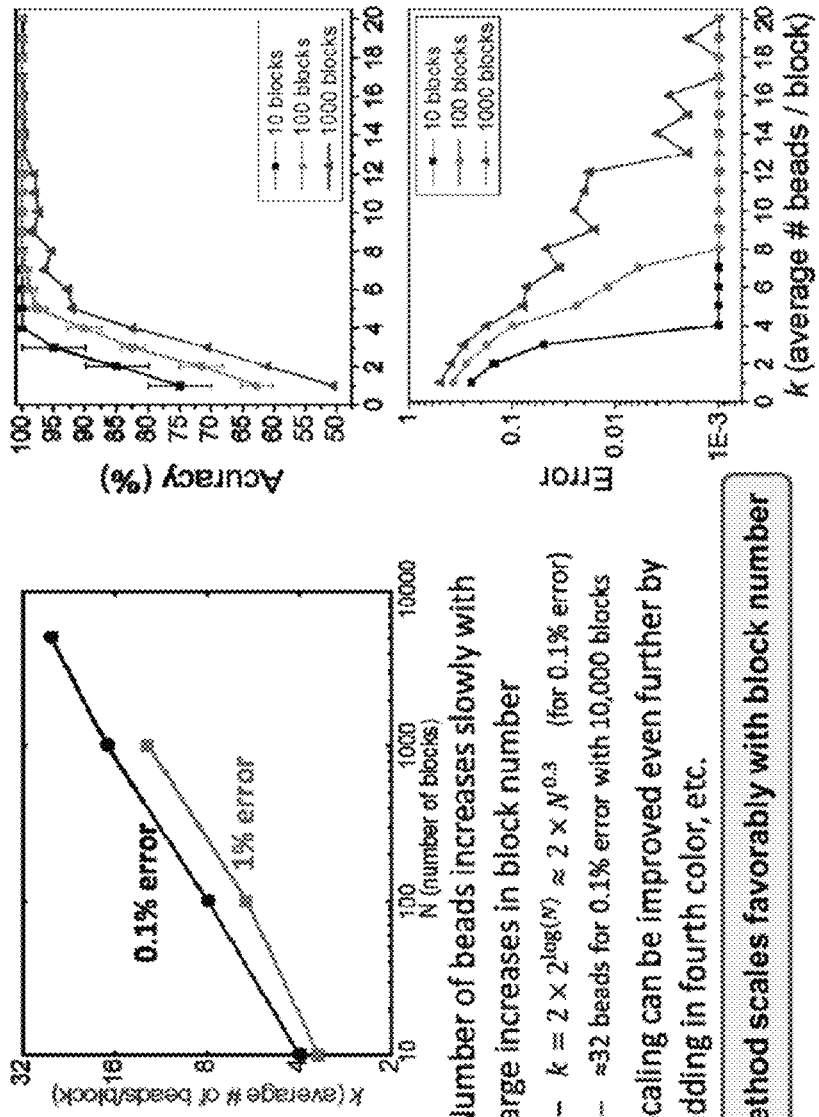
FIG. 20 depicts how the stochastic barcoding method favorably scales to large block numbers.
Figure 21:
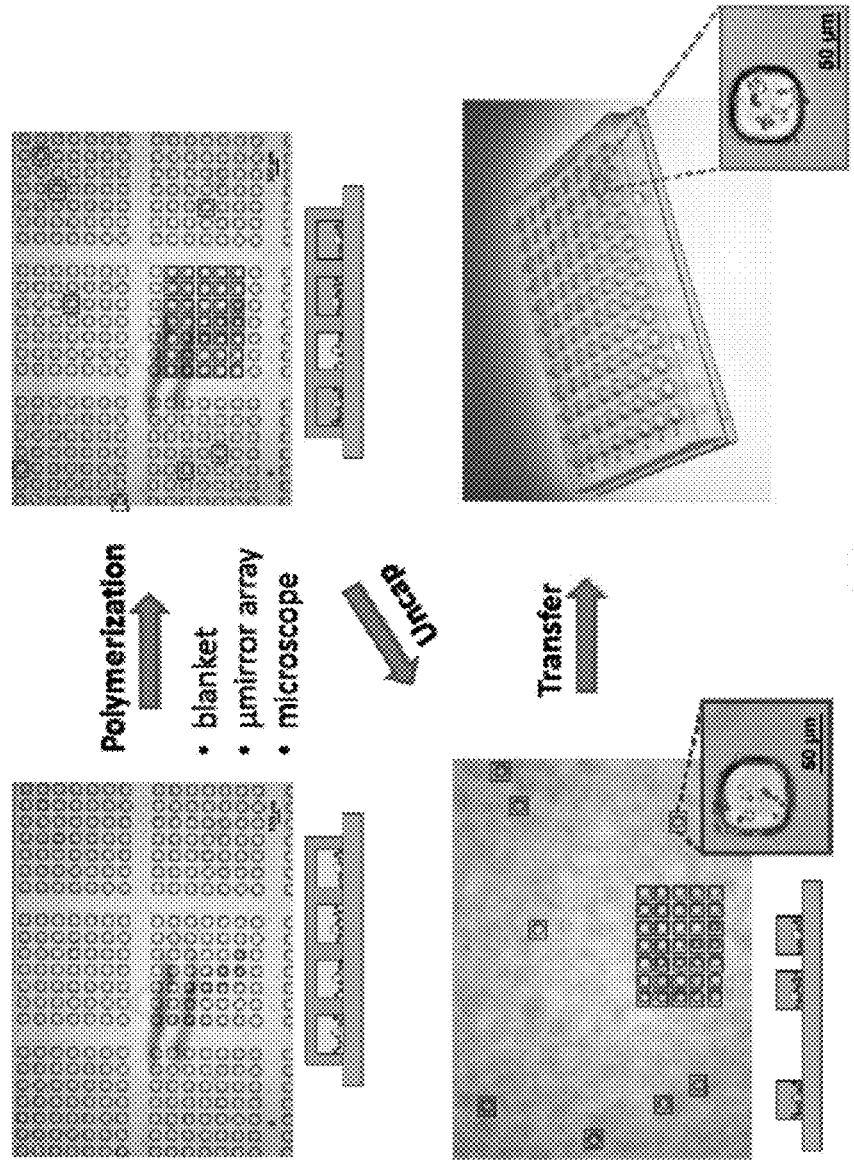
FIG. 21 illustrates imaging and matching cell blocks.

The accuracy of the stochastic barcoding model was considered in light of certain variables including bead number, missing beads, number of colors, as shown in FIG. 17. For example, 100 blocks with three bead colors and +/−5 um bead movement with a bead loss of k/4 and no block loss yielded a 1% error rate when using 7 beads per block as opposed to a 0.1% error rate when 8 beads per block were used. This data demonstrated that scaling of cell blocks is promising using stochastic barcoding modeling. FIG. 18 shows the practical limit in case of low number of beads per block. Even though the theoretical code depth is much larger than the number of blocks to be labeled, since the number of beads distribution per block follows a Poisson distribution, at low k values there is a chance of having blocks with no beads or just one bead, which can led to a mismatch in the block identification. As shown in FIG. 19, the modeling demonstrated that block loss affects accuracy at small numbers of beads per block (k) but that the method is insensitive to block loss at large k values. Accordingly, accuracy may be maintained by either increasing the k value or decreasing block loss. Specifically, when scaling the stochastic barcoding method to larger block numbers, the number of beads must also increase slowly with large increases in block number as shown in FIG. 20. For example, for 10,000 blocks, 32 beads per block must be used to maintain an error rate of 0.1%.

Figure 22:
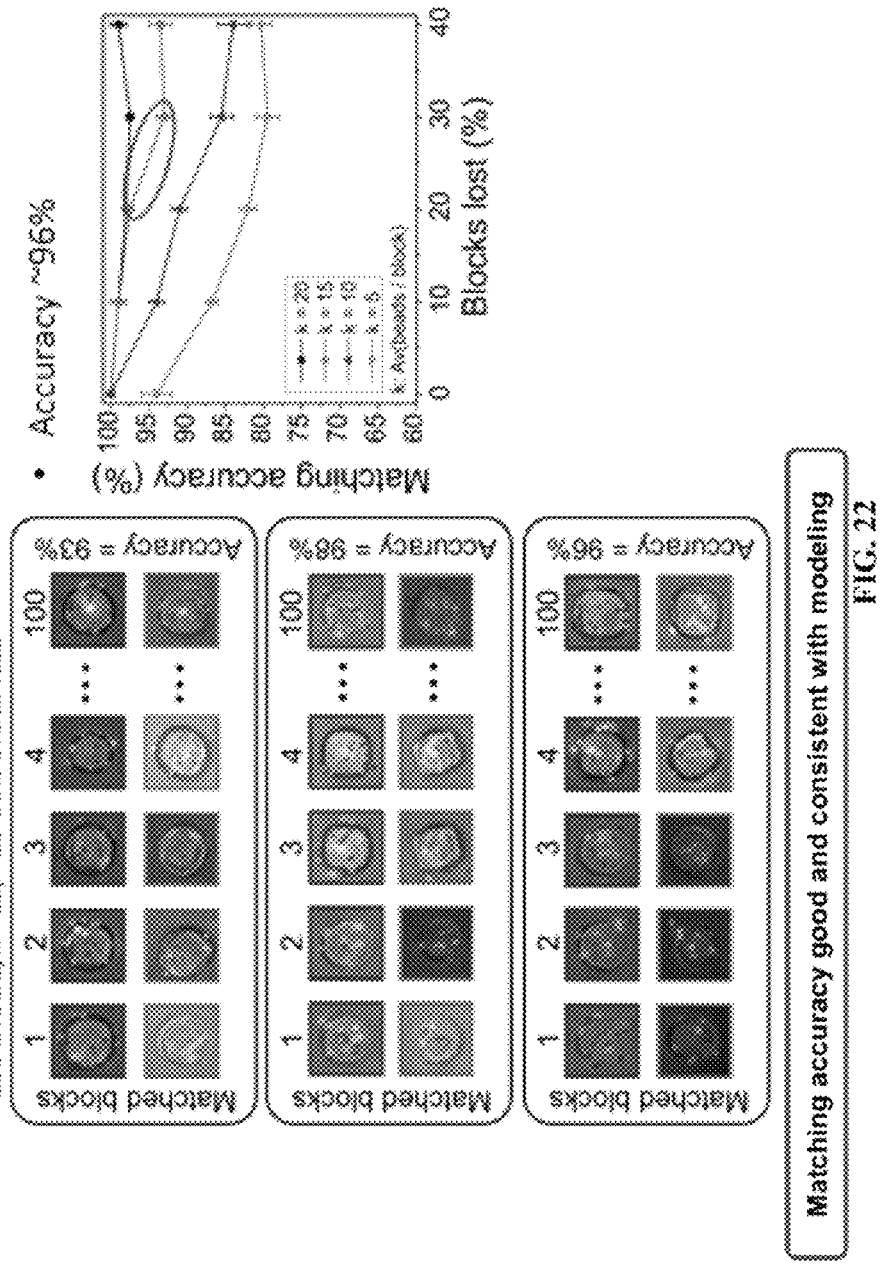
FIG. 22 depicts a completed imaging and matching process for 100 blocks and determines that matching accuracy is consistent with the modeling.

Three sets of experimental data demonstrate that the matching accuracy is consistent with the modeling, as shown in FIG. 22. Using an average of fifteen beads per block in 100 total blocks with a block loss between 20 and 30%, the accuracy of matching ranged was 93%, 96% and 98% for the three experimental sets.

Figure 23:
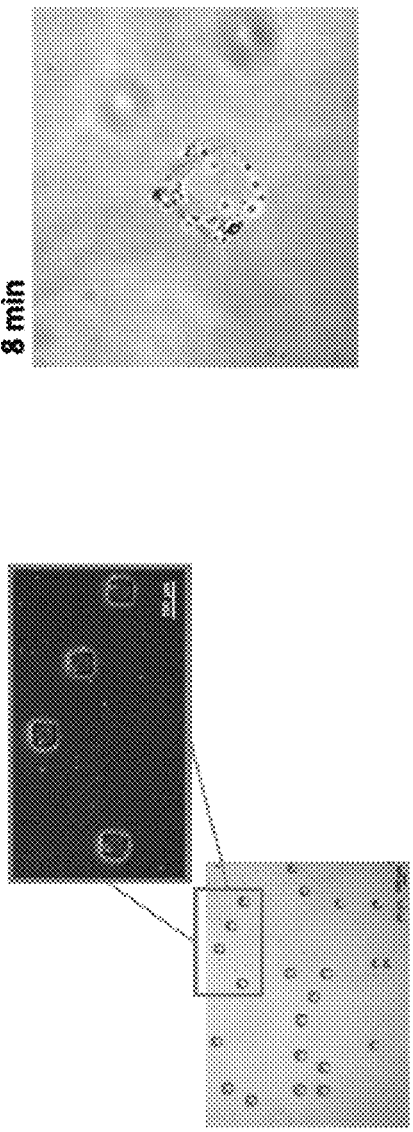
FIG. 23 illustrates how the cells are recovered from the photopolymerized blocks.
Figure 24:
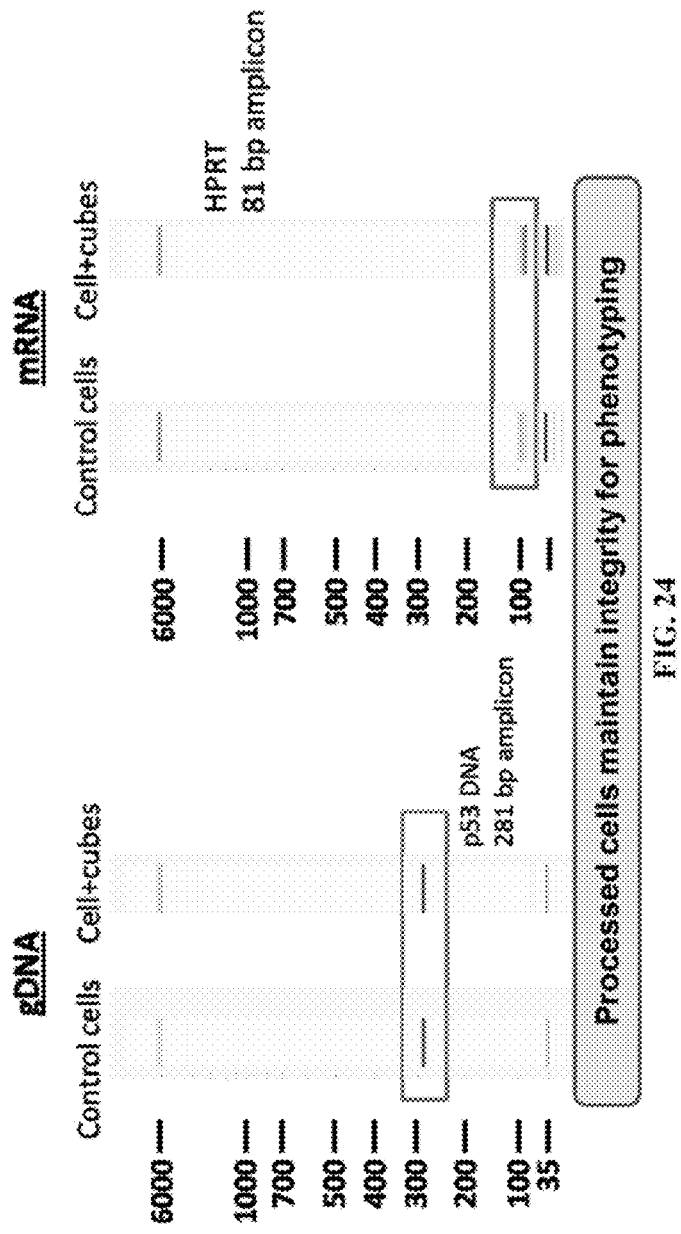
FIG. 24 determines that recovered cells maintain integrity for phenotyping.
Figure 25:
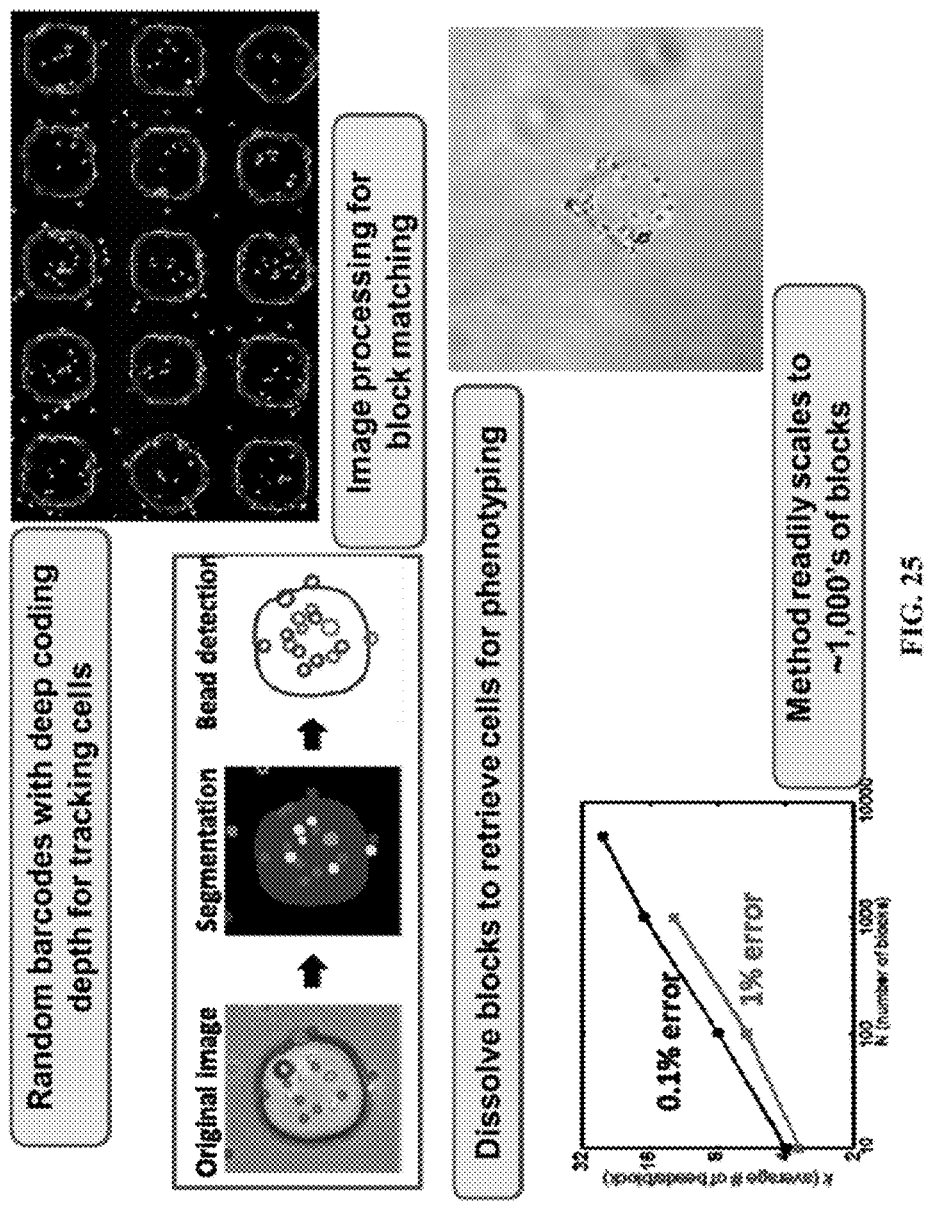
FIG. 25 concludes that stochastic barcodes provide deep coding depth for tracking cells and that this method readily scales to 1,000 s of cell blocks.

Recovering cells from the blocks was successfully accomplished using collagenase to depolymerize the photo-polymerized hydrogel blocks as shown in FIG. 23. Using PCR of genomic DNA and mRNA from depolymerized cell-laden blocks and comparing to control cells demonstrated that the processed cell maintain integrity for phenotyping, as shown in FIG. 24.

Modeling the SPB Process

Figure 31A:
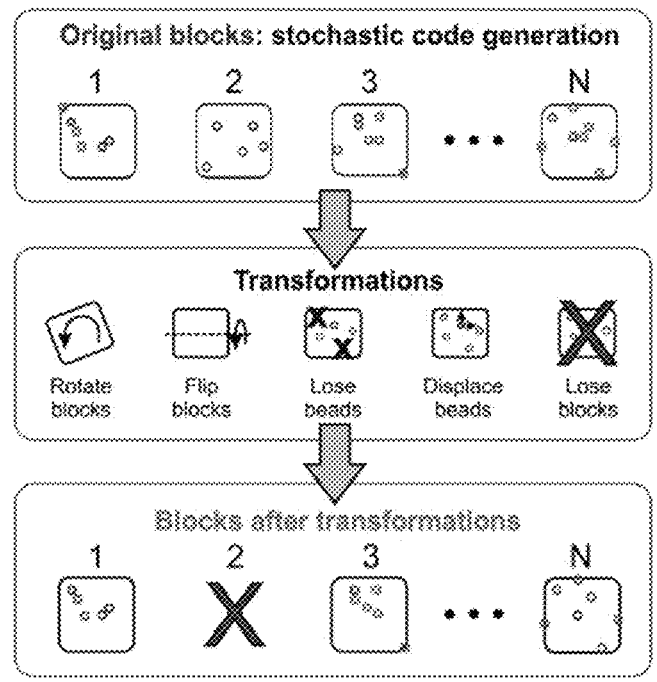
FIGS. 31A-31B depict depicts Monte Carlo simulations of the block matching process and the effect of process variables.
Figure 31B:
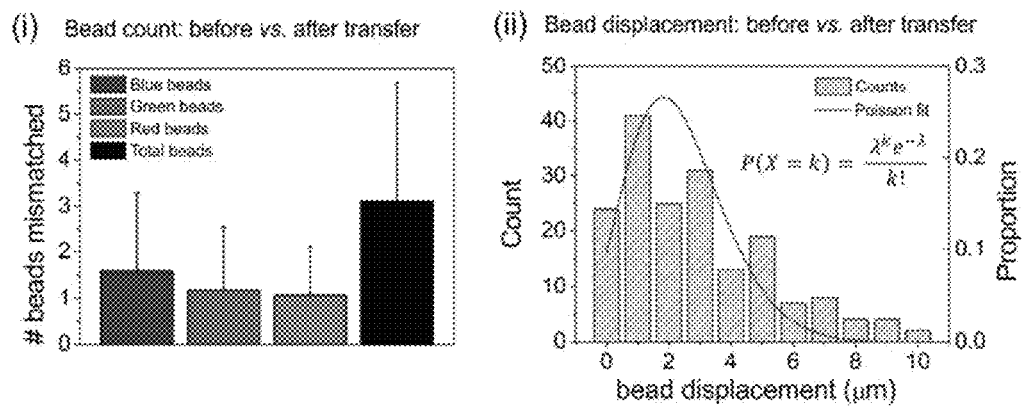

A Monte Carlo model of the SPB process can be used to understand how the accuracy of the block matching process is affected by different parameters of the method (i.e., bead number, missing beads, number of colors, block loss, etc.). The model computationally generated different numbers of blocks of a given size and with probabilistic distributions of the number, color and 2D locations of beads to simulate the first set of images from the blocks before transfer (FIGS. 31A-31B). Then, the model applies the same transformations experimentally observed occurring to the transferred blocks (i.e., bead loss, bead movement within the block, block loss during the transfer process), producing a second set of images. The magnitude and distributions of those transformations were empirically derived from the experiments (FIG. 31B).

Figures 26A, 26B, 26C, 26D:
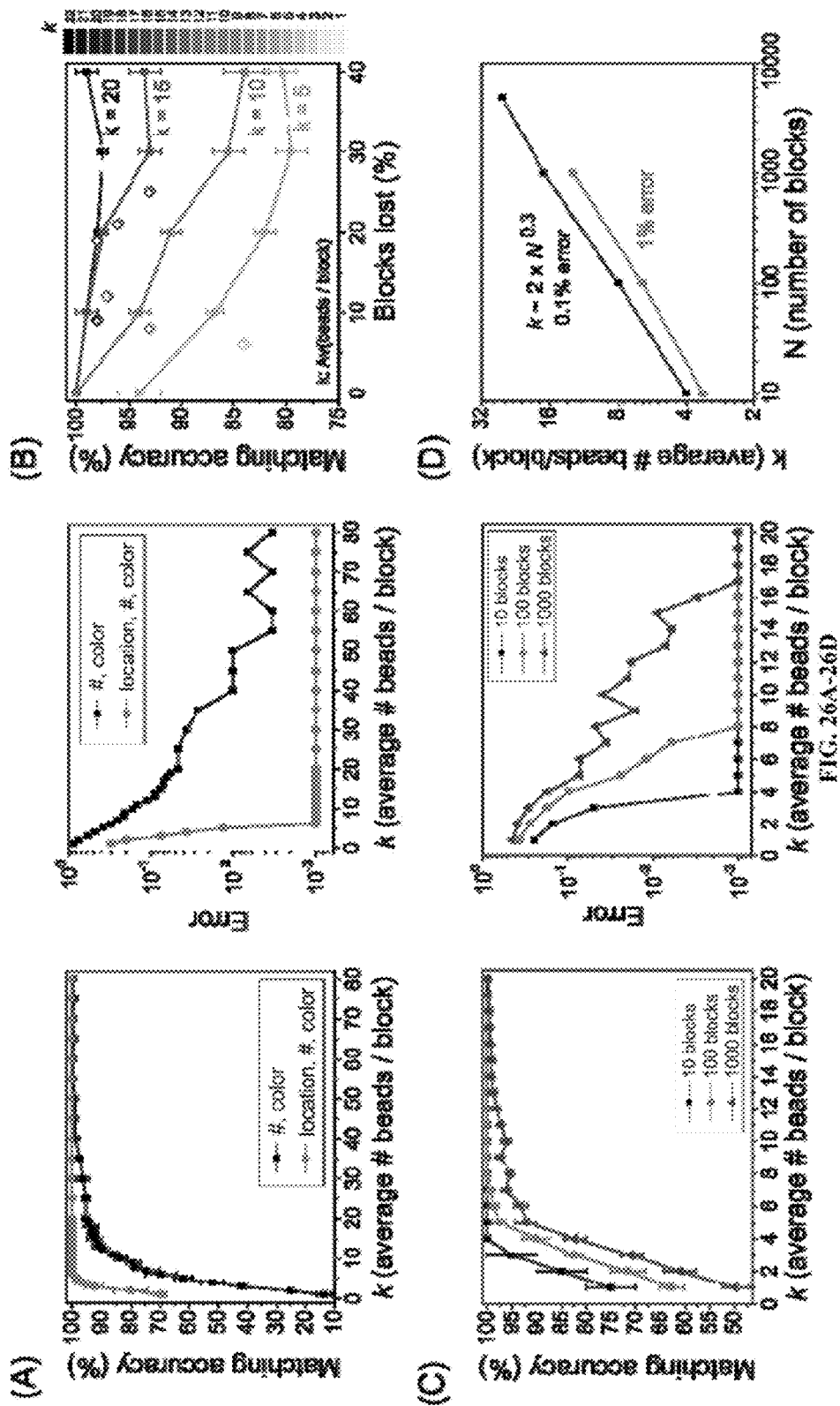
FIGS. 26A-26D depict SPB modeling.
Figures 32A, 32B:
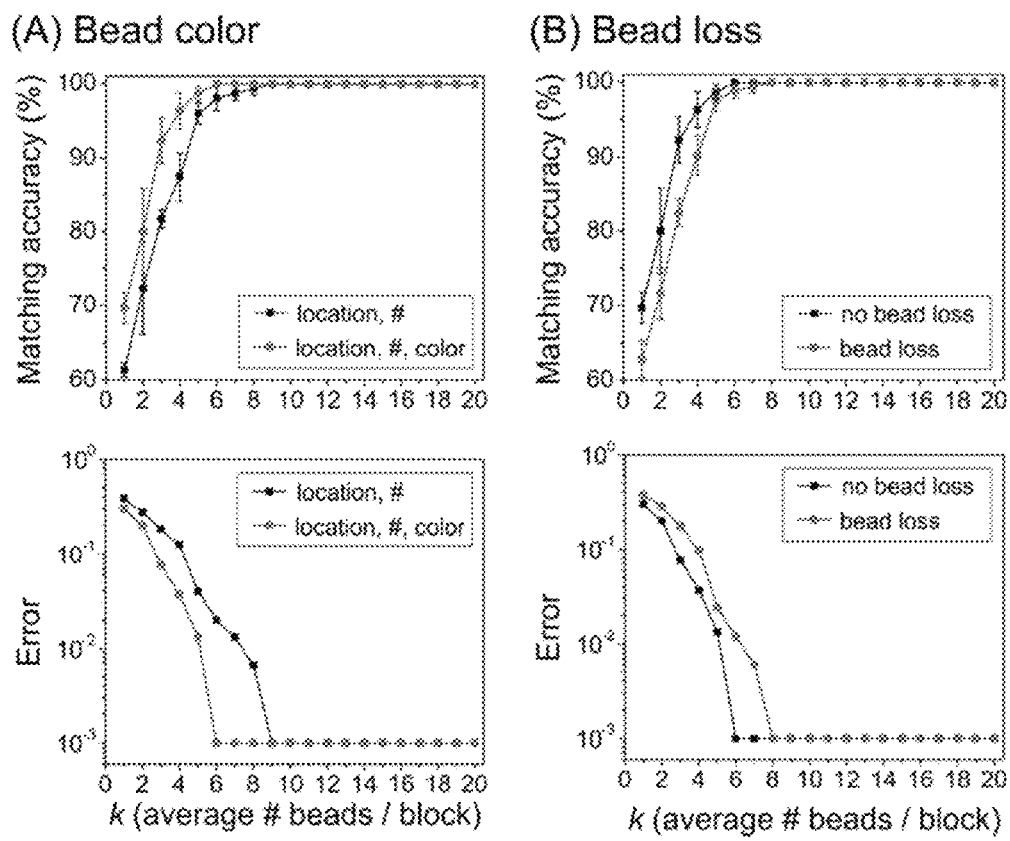
FIGS. 32A-32B depict dependence of block matching accuracy on SPB method parameters.

The Monte Carlo model was first used to computationally generate a series of 100 blocks to examine the importance of using bead location in the code relative to just using bead number and color. As expected, the model showed increasing matching accuracy as the average number of beads per block (k) increased (FIG. 26A). More interestingly, we observed dramatic improvement in block matching accuracy when bead location was used as part of the code rather than just the number and color of beads (FIG. 26A). For example, considering 100 blocks that need to be matched without any bead or block loss, an average of 6 beads per block was sufficient to obtain 0.1% matching error using bead location, number, and color as the code. In contrast, using only bead number and color required ~40 beads per block to obtain a 1% error. Bead color was also important. Using three colors instead of one substantially improved block matching accuracy (FIG. 32A), though it did not have as strong an influence as the location of the beads.

Beads can be lost (or gained) during block transfer, which subsequently affects accuracy. Comparing simulations where blocks can lose up to 25% of the beads in the block before transfer to simulations without any bead loss, we found a modest increase in the average number of beads per block was needed to maintain 0.1% error in block matching (i.e., two additional beads per block, FIG. 32B).

A more significant experimental parameter was the loss of blocks during the transfer process (either due to loss during pipetting or imaging failures). The model predicts that block matching accuracy decreases substantially with increasing block loss for small k values (FIG. 26B). For example, matching accuracy for k=5 beads per block, falls from 94% to 83% when increasing the percentage of blocks lost from 0% to 20%, respectively. The loss in matching accuracy becomes less important as k increases, and interestingly, the accuracy becomes insensitive to block loss for k≥15 beads per block (99% to 97% accuracy for k=15 for 0% of blocks lost and 20%).

To assess the validity of the model, matching experiments were performed with different values for k and amount of block loss, superimposing experimental results onto simulation results (FIG. 26B). Experiments qualitatively and quantitatively tracked the predictions from modeling. For instance, comparing the accuracies of block matching from the experimental results (96%) and the model (97%) for k=15 beads per block, with a 21% block loss and <25% bead loss, the relative difference between experiment and simulation was about 1%. These results confirm that increasing k (average number of beads per block) by 1 obtains high accuracies in block matching and good protection against the effects of block loss and bead loss. Thus, experimentally, one can improve desired performance by adding more beads/block, decreasing the loss of blocks during the procedure, or both.

One important criterion for a cell tracking method is scalability. The ideal method should be scalable to track 1000's of unique blocks, beyond the limit that most current single-cell analysis tools can handle. See, Chattopadhyay, P. K.; Gierahn, T. M.; Roederer, M.; Love, J. C., *Nat Immunol* 2014, 15 (2), 128-135, and Ogunniyi, A. O.; Story, C. M.; Papa, E.; Guillen, E.; Love, J. C., *Nat. Protocols* 2009, 4 (5), 767-782, each of which is incorporated by reference in its entirety. Scale-up of the SPB method was simulated and as expected, increasing average number of beads per block, k, is required to track increasing numbers of blocks to maintain a given accuracy (FIG. 26C). The required k scales approximately as $2 \times N^{0.3}$, where N is the number of blocks, suggesting that ~32 beads/block would be needed to track 10,000 blocks with a 0.1% matching error (FIG. 26D). This scaling is quite favorable, and can be improved even further by increasing the number colors, adding parameters to the code (bead size, for example), or decreasing desired accuracy. See, Fournier-Bidoz, S.; Jennings, T. L.; Klostranec, J. M.; Fung, W.; Rhee, A.; Li, D.; Chan, W. C. W., *Angewandte Chemie International Edition* 2008, 47 (30), 5577-5581, which is incorporated by reference in its entirety.

Figure 27A:
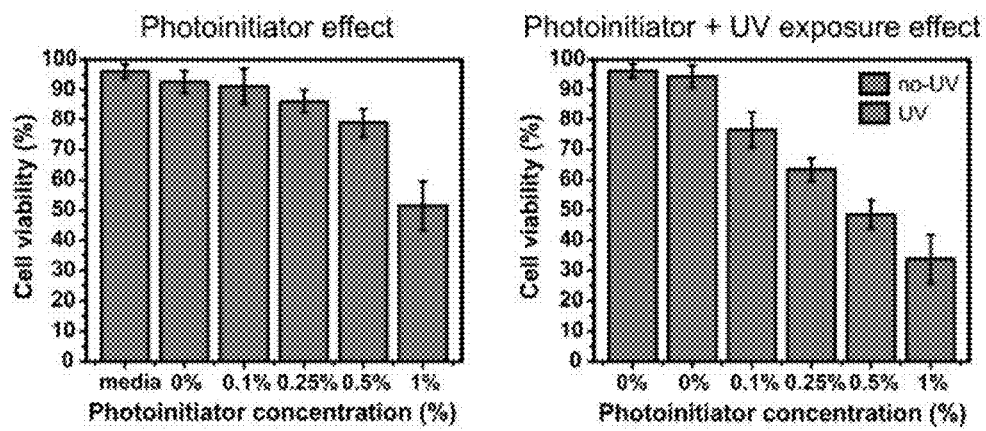
FIGS. 27A-27B depict recovery of nucleic acids and viable cells from stochastic barcoded, enzyme-degradable PEGDA blocks.
Figure 33:
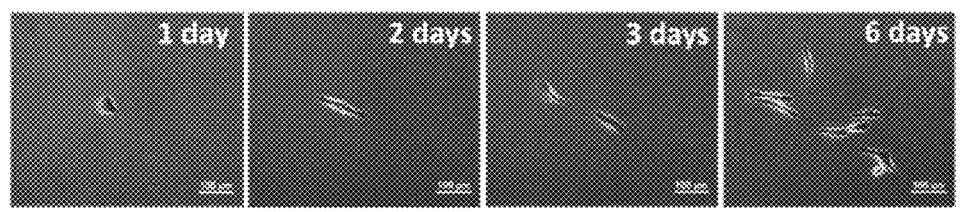
FIG. 33 depicts single cell proliferation after block isolation and digestion. A representative sequence of images showing outgrowth of a single viable cell isolated from a PEGDA block by collagenase degradation.

Viability of Cells and Recovery of Cellular Biomacromolecules from Barcoded Blocks As the final step in optimizing the SPB workflow, process variables were iterated that could affect cell viability during processing and recovery from hydrogel blocks. Viable cell isolation is crucial for the recovery of usable biological materials for downstream assays and single-cell or clonal growth, which are of broad interest for many biological applications, such as selecting yeast and bacteria for bioproduction and the analysis of various clonal populations in biology, such as B and T cells in immunology or circulating tumor cells in oncology. See, Panagiotou, V.; Love, K. R.; Jiang, B.; Nett, J.; Stadheim, T.; Love, J. C., *Applied and Environmental Microbiology* 2011, 77 (9), 3154-3156, Love, K. R.; Politano, T. J.; Panagiotou, V.; Jiang, B.; Stadheim, T. A.; Love, J. C., *PLoS ONE* 2012, 7 (6), e37915, Weiss-Ottolenghi, Y.; Gershoni, J. M., *FEBS Letters* in press, Nguyen, C. Q.; Ogunniyi, A. O.; Karabiyik, A.; Love, J. C., *PLoS ONE* 2013, 8 (3), e58127, Story, C. M.; Papa, E.; Hu, C.-C. A.; Ronan, J. L.; Herlihy, K.; Ploegh, H. L.; Love, J. C., *Proceedings of the National Academy of Sciences* 2008, 105 (46), 17902-17907, Miles, J. J.; Douek, D. C.; Price, D. A., *Immunol Cell Biol* 2011, 89 (3), 375-387, and Hayes, D. F.; Paoletti, C., *Journal of Internal Medicine* 2013, 274 (2), 137-143, each of which is incorporated by reference in its entirety. Notably, MWAs have been used to screen and clone cells, but the upper limit has remained approximately 100 cells per array by a manual recovery method. Conceivably, every well within the MWA could be encapsulated and isolated in a single workflow using SPB, providing an order of magnitude increase in the absolute number of events and reducing process time. Optimal conditions for SPB can be determined by quantifying the effects of photoinitiator concentration and UV exposure on cell viability. A murine melanoma cell line (B16F10) was used as a model cell type, and we found that photoinitiator concentrations up to 0.5% for 1 h still retained approximately 80% viability (FIG. 27A, left). Typically, the UV exposure time required to achieve single well photopolymerization at this photointiator concentration is 30 s to 1 min. The compound effect of UV exposure was examined for 2 min (twice the typical required time) and viability was maintained at approximately 50% in 0.5% Irgacure (FIG. 27A, right). Thus, these conditions (0.5% photoinitiator) were kept as a compromise between cell viability and photopolymerization time (30 s UV exposure/photopolymerization time). Finally, hydrogel blocks were photopolymerized with single cells, then blocks were manually picked for collagenase digestion and subsequent clonal outgrowth. B16F10 cells that retained their ability to grow and adhere were successfully isolated after undergoing the entire SPB and recovery method (FIG. 33). This result indicates that clonal populations can readily be selected, isolated, and grown out, greatly increasing the potential throughput for functional screening and subsequent cloning applications of the MWA platform.

SPB has the potential to enable integration of information on phenotypes obtained from microsystems (here, MWAs) with downstream applications (e.g., polymerase chain reaction, PCR; reverse transcription PCR, RT-PCR; clonal isolation and derivation). Many biological questions revolve around heterogeneity at the genetic level, and researchers often rely on these downstream analytical tools. To determine the suitability of the SPB process for isolating DNA and RNA following single-cell analytical analysis, we seeded MWAs with B16F10 cells at densities of approximately 1 cell per microwell. Subsequently, blocks were photopolymerized with acrylate-PEG-peptide-PEG-acrylate containing a collagenase-sensitive peptide sequence (GGG-PQGIWGQGK) (SEQ ID NO: 1), and an automated micromanipulator was used to visually verify and only hydrogel blocks with known contents (either empty or encapsulated single cells) were transferred into 96-well plates. Empty blocks served as negative controls and non-encapsulated cells were used as positive controls. All samples were processed in parallel with the same regimen of collagenase digestion and cellular lysis. Magnetic beads were added during lysis to capture nucleic acids released from the lysed cells, and beads were then processed to isolate genomic DNA or total RNA as described by the manufacturer's protocols.

Figure 27B:
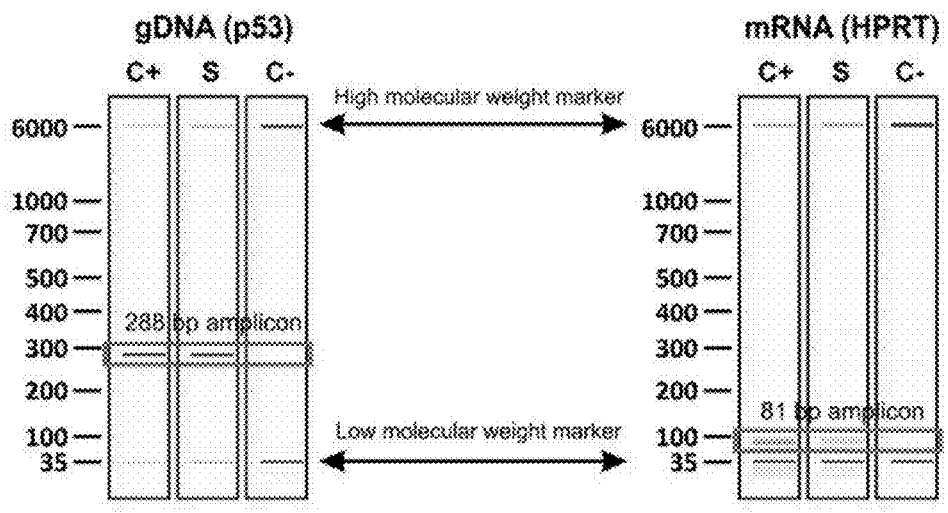

To evaluate the ability of SPB to recover intact DNA from coded cells, a micromanipulator was used to manually identify and collect groups of 5-10 blocks with single cells. Total genomic DNA was recovered from digested blocks and their content was transferred to microtiter plates containing a PCR reaction mixture with primers targeting a 288 base pair (bp) region of the gene encoding p53, the most commonly mutated tumor suppressor gene in human cancers. See, Olivier, M.; Hollstein, M.; Hainaut, P., *Cold Spring Harbor Perspectives in Biology* 2010, 2 (1), which is incorporated by reference in its entirety. As demonstrated in FIG. 27B, left, digestion of hydrogel blocks containing single B16F10 cells (lane S) produced a band of equivalent size as that generated from non-encapsulated cells used as a positive control (lane C+); digestion of hydrogel blocks without cells produced no bands (lane C−) indicating that the photopolymerization solution itself does not contain amplifiable genomic DNA (e.g., free DNA from dead cells).

RT-PCR is another commonly used assay that examines the expression level of genes within cells to phenotype gene regulatory networks. The integrity of hypoxanthine guanine phosphoribosyl transferase (HPRT) mRNA was examined for use in RT-PCR analyses. HPRT is a housekeeping gene frequently used to normalize RNA input in RT-PCR reactions, and is less abundant compared to other housekeeping genes such as glyceraldehyde-3-phosphate dehydrogenase. See, Foss, D. L.; Baarsch, M. J.; Murtaugh, M. P., *Animal Biotechnology* 1998, 9 (1), 67-78, which is incorporated by reference in its entirety. Blocks were isolated manually again via micromanipulator followed by hydrogel block digestion and cell lysis as described above. Using exon-spanning primers designed for real time RT-PCR, successful amplification of HPRT mRNA (FIG. 27B, right) was obtained from positive control cells (lane C+) and digested hydrogel blocks containing single cells (lane S) with no products detected in digested, empty hydrogel blocks (lane C−).

In summary, stochastic particle barcoding is a simple and scalable method for tracking cell identity across analytical platforms. The experimental data and modeling both demonstrate that random barcodes provide deep coding depth for tracking cells while also providing a scalable method to thousands of blocks. A software was developed to recover the identity of blocks and thus encapsulated cells after transferring between analytical platforms, with matching accuracy that was consistent and in agreement with simulations from a Monte Carlo model. The model also showed that SPB scales favorably with the number of beads per block for larger populations of blocks. Finally, the cells can be recovered by digesting the transferred polymer blocks with collagenase, and successfully recovered cells for genotyping, phenotyping, and clonal outgrowth. SPB therefore should enable the performance of multiparametric studies in sparse cell populations to improve our understanding of cellular heterogeneity across diverse biological fields and enhances the utility of many lab-on-a-chip type platforms.

EXAMPLES

Figures 34A, 34B:
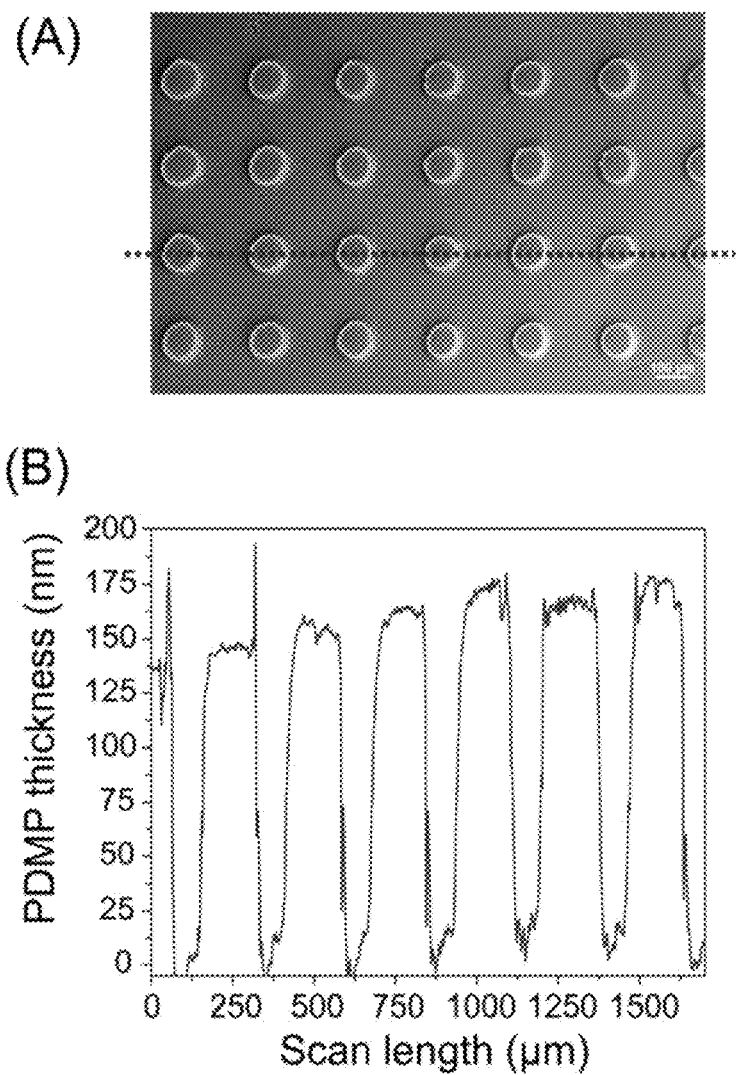
FIGS. 34A-34B depict PDMP characterization.

Polymer Solution Preparation:

PDMP coated glass slides: poly(2,2-dimethoxy nitrobenzyl methacrylate-r-methyl methacrylate-r-poly(ethylene glycol) methacrylate) (PDMP) was used a pH sensitive degradable sacrificial layer on top of the sealing glass slides for the PDMS microwell arrays. PDMP was synthetized according to the protocols described in Kim, M.; Choi, J.-C.; Jung, H.-R.; Katz, J. S.; Kim, M.-G.; Doh, J., *Langmuir* 2010, 26 (14), 12112-12118, which is incorporated by reference in its entirety. APTES glass slides (75×25 mm$^2$, 1 mm Thick, Surface Coated with APTES, Electron Microscopy Sciences) were spin coated adding 90 µL of a 7.5 wt % PDMP solution in 1,4-dioxane (Sigma-Aldrich) and spinning at 2000 rpm for 2 min. PDMP-coated slides were dried in vacuum overnight to enhance adhesion, and then exposed to ultra-violet (UV) light for 2 minutes (15 mW cm$^{-2}$ at 240-395 nm) to render the PDMP layer pH sensitive. Results from profilometer analysis (Dektak 150, Veeco) showed that the resulting PDMP layer was 150 nm thick (FIGS. 34A-34B).

PEGDA: Pre-polymer solutions containing 20% w/v 1 KDa PEGDA (Laysan Bio) and 1% catalase (Sigma) as anti-oxidant to improve cell viability and enhance photopolymerization were prepared in Hank's buffered saline solution (Gibco) adjusted to pH 6 with Hydrochloric acid (HCl). The solution was then vortexed and filtered with 0.8 µm PTFE filter (National Scientific).

Degradable peptide-PEGDA: Synthesis of peptide-PEGDA MW 8,000 was done by reacting acrylate-PEG-Succinimidyl Valerate (acrylate-PEG-SVA MW 3,400 Da, Laysan Bio) with the proteolytically degradable peptide sequence (GGGPQGIWGQGK) (SEQ ID NO: 1), similarly as described in Lee, S.-H.; Miller, J. S.; Moon, J. J.; West, J. L., *Biotechnology Progress* 2005, 21 (6), 1736-1741, which is incorporated by reference in its entirety. A solution of 1% catalase was prepared using HBSS at pH 6, vortexed and filtrated with 0.2 µm PTFE filter. Then, the pre-polymer solution of peptide-PEGDA was prepared using this filtered catalase solution, 20% w/v peptide-PEGDA MW 8,000.

Pre polymer solution for cell encapsulation: Consists of a mixture of 80% v/v PEGDA and 9% v/v degradable peptide-PEGDA of previous pre-polymer solution, 0.5% w/v photoinitiator (Irgacure 2959, Ciba), 4.4% v/v methanol, 6.6% v/v mixture of RGB fluorescent polystyrene latex 4.5 um beads at a concentration 5×10$^8$ particles mL$^{-1}$ (Fluoresbrite Microspheres YO-YG-BB, Polyscience Inc.).

Cells: B16F10 murine melanoma cells were cultured at 37° C. in 5% CO2 and 95% relative humidity. Cells were passaged every 2-3 days in Dulbecco's Modified Eagle Medium (DMEM) supplemented with 10% fetal bovine serum and penicillin/streptomycin. Healthy human peripheral blood mononuclear cells were obtained from Research Blood Components (Brighton, Mass.) under a protocol exemption approved by the Committee on the Use of Humans as Experimental Subjects at MIT. Briefly, healthy human peripheral blood was centrifuged for 25 min at room temperature over a density gradient (Ficoll-paque PLUS; GE Healthcare Life Sciences). PBMCs were harvested and used fresh in RPMI1640 supplemented as above or frozen in 90% FBS/10% DMSO for future use.

Peptide-PEGDA solution: Mix 500 uL HBSS at pH 6 and 5 mg of catalase in an Eppendorf tube, and vortex the mixture for 1 minute. Use 1 mL syringe with needle to take 500 uL of the catalase solution, filter the catalase solution with 0.2 um PTFE filter into a new Eppendorf tube, and vortex. Take 100 uL of this filtered solution to mix with 20 mg of lyophilized peptide-PEGDA 3400 or peptide-PEGDA1000 in an Eppendorf tube, and vortex. A peptide-PEGDA solution with 20% polymer and 1% catalase was prepared.

PEGDA1000 solution: mix 200 mg of standard PEGDA1000 (Laysan Bio) and 10 mg of catalase in an Eppendorf tube. Then add 1 mL HBSS at pH 6 into the Eppendorf tube and vortex for 1 minute. The Eppendorf tube was placed at 37° C. for 2 minutes and vortex again. The Eppendorf tube was then centrifuged 5 minutes @ 4000 rpm. Supernatant was recovered with 1 mL syringe and a needle. The PEGDA1000 and catalase solution was filtered with 0.8 um filter. The PEGDA1000 solution with 20% polymer and 1% catalase was prepared.

Photo-initiator solution: Mix 250 mg Irgacure 2959 and 1 mL pure methanol in an Eppendorf tube, and vortex for 1 minute or until it is totally dissolved.

Final polymer mix solution: Mix 88 uL of peptide-PEGDA and 12 uL of PEGDA1000 solutions in an Eppendorf tube, and add 2.5 uL of Irgacure2959 solution into the Eppendorf tube. RGB beads (4.5 um beads Polyscience Inc, at 5E8 beads/mL)—2 uL red beads, 2 uL green beads, 2 uL blue beads—were added for coding. Add 16.5 uL cells solution at 2E6-2E7 cells/mL (depending on desired final concentration). Final solution includes about 14% peptide-PEGDA, 2% PEGDA1000, 0.8% catalase, and 0.5% Irgacure 2959.

Polymerization Process:

Place ⅙ of 65 um no channels MWA polydimethylsiloxane (PDMS) device (MWA devices from Love lab) on a glass slide. The device on the glass slide was put it in plasma cleaner for 2 minutes of vacuum followed by 15 minutes of plasma oxidation at high RF. Right after plasma oxidation, 40 uL of final polymer mix solution was quickly added on top of MWA devices. Wait 2 minutes for cell sedimentation into wells. Cover with APTES glass spin coated with a poly(2,2-dimethoxy nitrobenzyl methacrylate-methyl methacrylate-r-poly(ethylene glycol) methacrylate) (PDMP) sacrificial layer, and wipe excess of polymer solution surrounding PDMS. PDMP was synthesized according to Kim, et al. *Langmuir* 2010, 26(14), 12112-12118, which is incorporated by reference in its entirety. Sandwich device was flipped over to let trapped cells into the well sediment onto APTES glass cover.

Device is now ready for UV exposure. The process can be direct UV writing or flash exposure. Direct UV writing procedure includes placing sandwich device on microscope stage, using inverted microscope with Dapi filter (or no filter→all spectrum of EXFO X-Cite 120 light source) at desired magnification and adjusting area of exposure with mechanical diaphragm in the light path, which can be adjusted up to 40 um features with 40× objective and closed diaphragm, exposing for a period of time based on Irgacure 2959 concentration (typically <1 minute for 0.5% photoinitiator), and using an XY stage to photopolymerize desired wells with cells of interest. Flash exposure includes using a set-up with EXFO X-Cite 120 light source with a light guide coupled to a collimator +45° mirror, placing sandwich device on the stage, and exposing for <1 minute, at approximately 16 mW/cm$^2$.

After UV exposure, APTES cover slide was gently peeled off to transfer polymerized blocks from PDMS to APTES glass. APTES slide was placed into a Petri dish with 20 mL HBSS at pH 6, and gently agitated with tweezers to wash any floating cells or polymer left-overs.

Imaging and Block Transferring

Image all transferred blocks on APTES glass (i.e., bright field+all fluorescent channels required to get signal from coding beads—usually RGB). Take slide and wipe media around transferred features. Delimit the area of transferred polymer blocks with a hydrophobic pen, for example, by drawing a pool around transferred blocks region. 200 uL of HBSS and 1% BSA at pH7 were added to dissolve PDMP sacrificial layer underneath the transferred blocks. A cell scraper was used to gently resuspend the blocks and then transfer them into microtiter plate. Warm media (DMEM, High glucose, L-Glutamine, 10% BCS, and 1% PenStrep) was added to fill the wells in the microtiter plate. Single blocks were imaged in the microtiter plate before next cell analysis. Custom Matlab script was used to take the images sets, and to apply image processing to identify codes on blocks and then find best matching to recover block ID.

Peptide-Polymer Digestion with Collagenase

Supernatant was removed from the wells with single blocks in the microtiter plate, and 200 uL of filtered collagenase Type 1 at 4000-8000 U/mL was added. Polymer should dissolve within 10-40 minutes at RT; agitation and 37° C. can enhance polymer digestion.

gDNA Isolation from Peptide-PEGDA Polymer Cubes Containing B16F10 Cells:

Cells were collected after collagenase digestion into Eppendorf tube. The tube was spun down for 5 min, 2000× g. MagMax-96 RNA lysis buffer (200 uL of 1×=180 uL lysis buffer concentrate+220 uL isopropanol) was added to the tube. Then, add 20 uL of SPRI beads (gDNA), and vortex. Rotate the tube at room temp for 5-10 min, and wash in magnetic bead stand (Invitrogen) with 70% EtOH as described in Agencourt AMPure XP SPRI beads. Eluted using Endofree TE (20 uL) by vortexing and pipetting magnetic beads, transferred to another lobind tube while on magnetic stand, and transferred 20 uL to PCR tube. Then PCR.

p53 mouse A and B primers were resuspended (22.1 and 21.9 nmol into 1.105 and 1.095 mL nuclease free water). 3 samples were prepared. In general 3 samples means there are:

1. Positive control: cells with no polymer solution
2. Negative control: empty polymer cubes with no cells
3. Sample: polymer cubes with cells encapsulated In each case, 20 uL are taken.

PCR recipe (30 μL reaction) can include 20 μL gDNA per reaction, and 10 μL primer/NTP/Enyzme mix per reaction. The PCR recipe can include 10× buffer=3 μL per reaction×3=9 μL, 10 mM dNTP=0.6 uL per reaction×3=1.8 μL, 50 mM MgSO4=0.9 μL per reaction×3=2.7 μL, 20 μM p53 primer A=0.375 per reaction×3=1.125 uL, 20 uM p53 primer B=0.375 per reaction×3=1.125 μL, HiFi Platinum Taq (Invitrogen)=0.3 μL per reaction×3=0.9 μL, total=16.65 μL reaction components+13.35 μL H2O=10 μL per reaction×3=30 μL.

After pipette mixing 20 times into each of 3 samples, 10 μL master mixture was aliquoted. A PCR cycle can include 94° C. for 2 minutes, then 94° C. for 30 seconds, then 58° C. for 1 minute, 68° C. for 1 minute, then repeating 45 cycles of 94° C. for 30 seconds, then 72° C. for 5 minutes, and then holding at 4° C. Next day, samples were submitted to BioMiro core for Agilent bioanalyzer, 2 μL for each reaction.

Microwell Arrays:

Arrays of microwells comprising 50 μm cubic wells (84,672 wells/array) were prepared on 75×25 mm$^2$ glass slides (Corning) following previously reported protocols in Yamanaka, Y. J.; Szeto, G. L.; Gierahn, T. M.; Forcier, T. L.; Benedict, K. F.; Brefo, M. S. N.; Lauffenburger, D. A.; Irvine, D. J.; Love, J. C., *Analytical Chemistry* 2012, 84 (24), 10531-10536, which is incorporated by reference in its entirety. To fabricate the arrays, the silicone elastomer poly(dimethylsiloxane) (PDMS) (Sylgard 184 Silicone Elastomer Kit, Dow Corning) was mixed at a 10:1 ratio of base:catalyst, degassed under a vacuum at room temperature for 1 h, and then injected into a mold containing a microfabricated silicon master. The PDMS was cured at 80° C. for 4 h and subsequently released from the mold to produce a glass slide-backed array of microwells. Shortly before use, the arrays of microwells were treated with oxygen plasma (Plasma Cleaner PDC-001, Harrick Plasma) for 15 min to sterilize the array, turn the PDMS hydrophilic, and oxidize the array surface to enhance photopolymerization of PEGDA hydrogels.

Cell Encapsulation and Block Imaging:

Microwells containing cells of interest and pre-polymer solution with beads are photopolymerized by direct UV writing using Nikon Eclipse TiE inverted microscope fitted with a florescent light source (X-Cite 120, EXFO), an UV-2E/C excitation filter block (Nikon), and Photometrics CoolSnap HQ2 CCD camera. The combination of a 40× magnification (CFI S Plan Fluor ELWD 40× objective, Nikon) combined with a diaphragm allows to adjust the UV exposure area to the size of a single microwell (i.e., 65×65 μm$^2$). Automated XY motorized stage (BioPrecision2, Ludl Electronics) permits to move along the MWA photo-polymerizing only those microwells with the cells of interest. Polymerization time for given photoinitiator concentration is about 30 seconds for a given UV light intensity of 20 mW cm$^{-2}$ (measured with UVA meter, Control Company). Microscope and its parts were controlled with NIS-Elements Ar software (Nikon). Images of the blocks before and after transfer into the microtiter plates were done with same microscope and objective using filter sets UV-2E/C (Nikon), ET GFP and ET dsRED (Chroma), controlled with same previous software.

Manual Block Recovery via Capillary Micromanipulator:

An AVISO CellCelector robot (Automated Lab Solutions, software version 2.8; Jena, Germany) was used for picking of hydrogel cubes. A 96-well plate containing polymer cubes was placed on the deck of the microscope. The CellCelector software was then used for real time visualization and selective recovery of single-cell cubes. A glass capillary with an opening of approximately 150 μm was used to aspirate 1 μL of culture medium, then an additional 1 μL was aspirated to pick up each cube. Cubes were deposited into a 96-well collection plate, and the tool sensor was used to ensure that the tip touched to the bottom of the plate and that the entire 2 uL volume was dispensed. Borosilicate glass capillaries with an outer diameter of 1.5 mm and an inner diameter of 0.86 mm were pulled on the Sutter Instruments Flaming/brown micropipette puller, model P-1000 (Novato, Calif.).

Polymer Digestion:

Transferred blocks with cells were digested with filtered collagenase Type 1 (Worthington Biochemical Corp.) by adding ¼ of the total sample volume at 4000-8000 U mL$^{-1}$ for 10-20 min at room temperature (agitation at 37° C. enhance polymer digestion). The digestion reaction was stopped by addition of 2× volume HBSS with 10 mM EDTA.

Nucleic Acid Isolation:

Cells were lysed in 1× MagMAX Lysis/Binding Solution (Life Technologies) in the presence of Agencourt AMPure XP magnetic beads (Beckman Coulter, Inc.) for gDNA isolation OR MagMAX-96 Total RNA Binding Beads (Life Technologies) for total RNA isolation. The lysis solution was mixed well and incubated under agitation/rotation for 5 min at room temperature. Beads were washed as described in the manufacturer's protocol for gDNA or RNA, using either a magnetic plate holder (Biotek) or microcentrifuge tube stand (Life Technologies) to retain beads during washes. RNA was digested with TurboDNase at room temperature for 15 min to remove contaminating gDNA. gDNA was eluted using Endofree TE (Qiagen) and RNA was eluted using the supplied MagMAX Elution Buffer (Life Technologies) followed by pipetting up and down to resuspend beads. Beads were immobilized magnetically as previously described and supernatants were transferred to DNA Lobind tubes (Eppendorf).

PCR and RT-PCR:

Primer sequences for p53 PCR were A: 5' CAC AAA AAC AGG TTA AAC CCA G 3' (SEQ ID NO: 2) and B: 5' AGC ACA TAG GAG GCA GAG AC 3' (SEQ ID NO: 3). Primers for HPRT mRNA were obtained from Life Technologies (Assay Mm01545399_m1) as a premixed 20× concentrated Taqman solution for real time RT-PCR. PCR (Platinum Taq, Life Technologies) and OneStep RT-PCR (Qiagen) master mixes were directly added to total eluted gDNA or RNA. PCR cycling parameters: 94° C. for 2 min followed by 45 cycles (94° C. for 30 s, 58° C. for 1 min, 68° C. for 1 min), followed by 72° C. for 5 min. RT-PCR cycling parameters: 50° C. for 30 min, 95° C. for 15 min followed by 45 cycles (94° C. for 1 min, 60° C. for 1 min, 72° C. for 1 min) followed by 72° C. for 10 min. Reaction products were stored at 4° C. and subsequently analyzed using an Agilent Bioanalyzer capillary electrophoresis system using DNA High Sensitivity assay (Agilent, Santa Clara, Calif.).

Other embodiments are within the scope of the following claims.

What is claimed is:

1. A method of tracking cell identity comprising:
    adding a polymer solution with a plurality of markers into a block of a single cell microwell arrays;
    encapsulating the single cell in a matrix including a plurality of markers; and
    imaging the encapsulated cell to create a stochastic barcode determined by number, color, and position of the markers within the matrix, wherein the stochastic barcode is assigned to the single cell.

2. The method of claim 1, wherein the markers include polymer beads.

3. The method of claim 2, wherein the polymer beads include emissive polymer beads.

4. The method of claim 2, wherein the polymer beads are colored.

5. The method of claim 4, wherein the number of colors is two to six.

6. The method of claim 4, wherein the number of colors is three.

7. The method of claim 4, wherein the number of colors is four.

8. The method of claim 1, wherein the matrix is a hydrogel.

9. The method of claim 1, further comprising:
    imaging of arrays to assign a random code based on the plurality of markers;
    transferring arrays into a microtiter plate; and
    imaging arrays after transfer to read the code.

10. The method of claim 9, wherein the random code is assigned based on the number, color, size, and/or position of markers in the matrix.

11. The method of claim 9, wherein the encapsulation step includes photopolymerizing or chemical polymerization or thermal polymerization.

12. The method of claim 9, wherein assigning a random code includes using a machine learning algorithm.

13. The method of claim 9, wherein the markers include polymer beads.

14. The method of claim 13, wherein the polymer beads include emissive polymer beads.

15. The method of claim 14, wherein the polymer beads are colored.

16. The method of claim 15, wherein the number of colors is two to six.

17. The method of claim 15, wherein the number of colors is three.

18. The method of claim 15, wherein the number of colors is four.

19. The method of claim 9, wherein the matrix is a hydrogel.

20. The method of claim 13, wherein approximately one hundred cells in an array may be uniquely coded with an average of eight beads per encapsulated cell.

21. The method of claim 20, wherein an average of fifteen beads per encapsulated cell yields an approximate 100 percent matching accuracy.

22. The method of claim 9, wherein an average of fifteen beads per encapsulated cell yields an approximate 90 percent matching accuracy for one thousand cells.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Pro Gln Gly Ile Trp Gly Gln Gly Lys
1               5                   10

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacaaaaaca ggttaaaccc ag                                              22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 3
agcacatagg aggcagagac                                                   20

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acrylate-PEG
<220> FEATURE:
<223> OTHER INFORMATION: C-term PEG-acrylate

<400> SEQUENCE: 4

Gly Gly Gly Pro Gln Gly Ile Trp Gly Gln Gly Lys
1               5                   10
```